(12) United States Patent
Pingali et al.

(10) Patent No.: US 8,822,414 B2
(45) Date of Patent: Sep. 2, 2014

(54) HETEROCYCLIC COMPOUNDS SUITABLE FOR THE TREATMENT OF DYSLIPIDEMIA

(75) Inventors: Harikishore Pingali, Gujarat (IN); Pankaj Makadia, Gujarat (IN); Vrajesh Pandya, Gujarat (IN); Sairam Kalapatapu, V.V.M., Gujarat (IN); Mukul R. Jain, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 0 days.

(21) Appl. No.: 13/976,598

(22) PCT Filed: Dec. 26, 2011

(86) PCT No.: PCT/IN2011/000888
§ 371 (c)(1),
(2), (4) Date: Jun. 27, 2013

(87) PCT Pub. No.: WO2012/090220
PCT Pub. Date: Jul. 5, 2012

(65) Prior Publication Data
US 2013/0281366 A1 Oct. 24, 2013

(30) Foreign Application Priority Data
Dec. 28, 2010 (IN) .......................... 3556/MUM/2010

(51) Int. Cl.
| | |
|---|---|
| A61K 38/28 | (2006.01) |
| A61P 5/50 | (2006.01) |
| C07D 409/12 | (2006.01) |
| C07D 413/12 | (2006.01) |
| A61K 31/404 | (2006.01) |
| A61K 31/422 | (2006.01) |
| A61K 45/06 | (2006.01) |
| C07D 215/06 | (2006.01) |
| C07D 405/12 | (2006.01) |
| A61K 31/506 | (2006.01) |
| A61K 31/4433 | (2006.01) |
| A61K 31/4155 | (2006.01) |
| A61K 31/541 | (2006.01) |
| C07D 263/38 | (2006.01) |
| A61K 31/5377 | (2006.01) |
| C07D 309/04 | (2006.01) |
| A61K 31/4709 | (2006.01) |
| C07D 213/64 | (2006.01) |
| A61K 31/351 | (2006.01) |
| C07D 209/32 | (2006.01) |
| A61K 31/381 | (2006.01) |
| C07D 309/06 | (2006.01) |
| C07D 239/28 | (2006.01) |
| A61K 31/137 | (2006.01) |

(52) U.S. Cl.
CPC ............ *C07D 309/04* (2013.01); *C07D 409/12* (2013.01); *C07D 413/12* (2013.01); *A61K 31/404* (2013.01); *A61K 31/422* (2013.01); *A61K 45/06* (2013.01); *C07D 215/06* (2013.01); *C07D 405/12* (2013.01); *A61K 31/506* (2013.01); *A61K 31/4433* (2013.01); *A61K 31/4155* (2013.01); *A61K 31/541* (2013.01); *C07D 263/38* (2013.01); *A61K 31/5377* (2013.01); *A61K 31/137* (2013.01); *A61K 31/4709* (2013.01); *C07D 213/64* (2013.01); *A61K 31/351* (2013.01); *C07D 209/32* (2013.01); *A61K 31/381* (2013.01); *C07D 309/06* (2013.01); *C07D 239/28* (2013.01)
USPC .......................................................... 514/6.5

(58) Field of Classification Search
CPC ............................ A61K 31/137; A61K 31/16
See application file for complete search history.

(56) References Cited

U.S. PATENT DOCUMENTS

2010/0145052 A1   6/2010  Toyooka et al.

FOREIGN PATENT DOCUMENTS

WO    WO 2008035359 A2 *  3/2008

OTHER PUBLICATIONS

Miyamoto S: "Recent Advances in Aldose reductase Inhibitors: Potential Agents for the Treatment of Diabetic Complications", Expert Opinion on therapeutic Patents, Informa Haelthcare, GB, vol. 12, No. 5, Jan. 1, 2002, pp. 621-631, XP008010045, ISSN: 1354-3776, DOI; 10. 1517/13543776.12.5.621.

* cited by examiner

*Primary Examiner* — Marcela M Cordero Garcia
*Assistant Examiner* — Kaipeen Yang
(74) *Attorney, Agent, or Firm* — Renner Kenner Greive Bobak Taylor & Weber

(57) ABSTRACT

The present invention relates to compounds of the general formula (I), their tautomeric forms, their stereoisomers, their pharmaceutically acceptable salts, pharmaceutical compositions containing them, methods for their preparation, use of these compounds in medicine and the intermediates involved in their preparation. The present invention is directed towards compounds which can be used to treat diseases such as Hyperlipidemia and also have a beneficial effect on cholesterol.

(I)

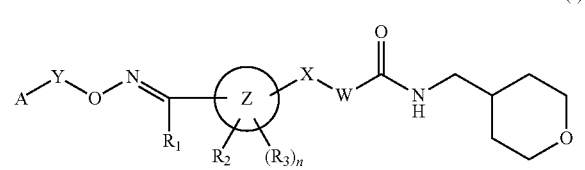

16 Claims, No Drawings

HETEROCYCLIC COMPOUNDS SUITABLE FOR THE TREATMENT OF DYSLIPIDEMIA

FIELD OF INVENTION

The present invention relates to compounds of the general formula (I), their tautomeric forms, their stereoisomers, their pharmaceutically acceptable salts, pharmaceutical compositions containing them, methods for their preparation, use of these compounds in medicine and the intermediates involved in their preparation.

The present invention is directed towards compounds which can be used to treat diseases such as Hyperlipidemia and also have a beneficial effect on cholesterol.

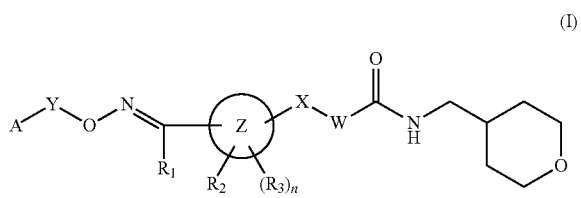

The compounds of the general formula (I) lower blood glucose, lower or modulate triglyceride levels and/or cholesterol levels and/or low-density lipoproteins (LDL) and raises the high-density lipoproteins (HDL) plasma levels and hence are useful in combating different medical conditions, where such lowering (and raising) is beneficial. Thus, it could be used in the treatment and/or prophylaxis of obesity, hyperlipidemia, hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders.

These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

The compounds of the present invention can be useful as aldose reductase inhibitors; for improving cognitive functions in dementia, and in the treatment and/or prophylaxis of disorders such as psoriasis, polycystic ovarian syndrome (PCOS), cancer, osteoporosis, leptin resistance, inflammation and inflammatory bowel diseases, wound healing, xanthoma, pancreatitis, myotonic dystrophy, endothelial cell dysfunction and hyperlipidemia.

BACKGROUND OF THE INVENTION

Higher LDL cholesterol levels in the plasma increase cardiovascular risk and reduction in the levels of LDL would decrease CVD risk by a comparable percentage (PNAS, 2009, 106, 9546-9547). Clearance of LDL cholesterol from plasma is through the action of LDL receptors in the liver and LDL receptors are cell surface glycoproteins that bind to apoliporpotein B100 (apoB 100) on LDL particles with high affinity and mediate their endocytic uptake (Journal of Biological Chemistry, 2009, 284, 10561-10570). Defect in hepatic cholesterol clearance and elevated levels of plasma LDL cholesterol that result from the mutations cause familial hypercholesterolemia. Such mutations are identified in the human LDL receptor and later in apolipoprotein-B (Nature Structural and Molecular Biology, 2007, 14, 413-419). Recently, mutations within certain subtypes of the pro-protein convertase subtilisin/gene such as the subtype nine (hereinafter "the gene") were found to represent a third class of mutations associated with autosomal dominant hypercholesterolemia (ADH). The discovery, etiology and functions of this subtype gene is discussed in details in Nature Genetics, 2003, 34, 154-156, Trends in Biochemical Sciences, 2008, 33, 426-434 etc. Several missense mutations (S127R, D129G, F216L, D374H, D374Y) are associated with hypercholesterolemia and premature atherosclerosis (J Lipid Res. 2008, 49, 1333-1343). Loss-of-function mutations (R46L, L253F, A433T) lead to elevated receptor abundance, enhancing clearance of LDL cholesterol from the circulation and reducing cardiovascular risk (Nature Structural and Molecular Biology, 2007, 14, 413-419).

Detailed molecular mechanisms explaining the association of LDLR and the particular subtype gene and LDLR degradation is not very clear (Drug News Perspectives, 2008, 21, 323-330). Because of inhibition of LDLR recycling, number of LDL receptors on the cell surface are decreased and this increases plasma LDL levels (PNAS, 2009, 106, 9546-9547).

Various approaches for inhibiting this particular subtype gene are reported, including gene silencing by siRNA or antisense oligonucleotides, mAb disrupting protein-protein interactions or by peptides; all the above-mentioned strategies have shown lowering of LDL cholesterol which may be effective therapy for treating hypercholesterolemia (Biochemical Journal, 2009, 419, 577-584; PNAS, 2008, 105, 11915-11920; Journal of Lipid Research, 2007, 48, 763-767; PNAS, 2009, 106, 9820-9825). However, very little success has been reported in trying to inhibit this subtype gene by using small molecules. Such small molecule inhibitors has its obvious clinical and therapeutic benefit over the other approaches as discussed above. We herein disclose novel small molecules which have shown to inhibit this particular gene in in-vitro studies and therefore provides an alternate beneficial approach for treating patients in need of such therapy.

Preferred Embodiments of the Invention

An important object of the present invention is to provide novel substituted oximino derivatives represented by the general formula (I), their tautomeric forms, their stereoisomers, their pharmaceutically acceptable salts, and pharmaceutical compositions containing them or their mixtures thereof.

In an embodiment of the present invention is provided a process for the preparation of novel substituted oximino derivatives and their derivatives represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

In a further embodiment of the present invention is provided process for treatment of diseases such as dyslipidemia, hyperlipidemia etc. by providing therapeutically effective amount of the compounds of formula (I) or their pharmaceutically acceptable salts or their suitable pharmaceutical compositions.

The above and other embodiments are described in details hereinafter.

DETAILED DESCRIPTION OF THE INVENTION

Accordingly, the present invention relates to compounds of the general formula (I),

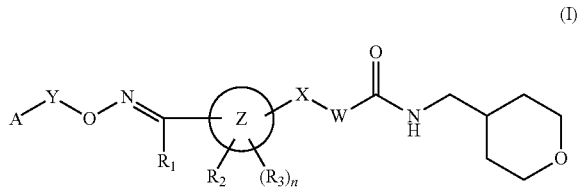

(I)

their tautomeric forms, their stereoisomers, their pharmaceutically acceptable salts, and pharmaceutical compositions containing them wherein 'A' represents an optionally substituted single or fused group selected from aryl, heterocyclyl or cycloalkyl groups;

In a preferred embodiment, 'A' is selected from optionally substituted aryl or heterocyclyl groups;

In a further preferred embodiment, the aryl group may be selected from substituted or unsubstituted monocyclic or bicyclic aromatic groups;

In a still further preferred embodiment, the aryl group is an optionally substituted phenyl group.

In an embodiment, when 'A' represents a heterocyclyl group, the heterocyclyl group may be selected from single or fused mono, bi or tricyclic aromatic or non-aromatic groups containing one or more hetero atoms selected from O, N or S;

In a preferred embodiment, the heterocyclyl group may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthyl idinyl, purinyl, carbazolyl, phenothiazinyl, phenoxazinyl, benzoxazolyl, benzothiazolyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl and the like;

'Y' represents either a bond or substituted or unsubstituted linear or branched ($C_1$-$C_6$)alkyl, ($C_2$-$C_6$)alkenyl groups or the groups represented by '—U(CH$_2$)$_m$—' wherein U represents O, S(O)$_o$, NR$_4$; 'm' represents integers from 2 to 4, 'o' represents integers from 0 to 2 and R$_4$ represents H, substituted or unsubstituted linear or branched ($C_1$-$C_6$)alkyl;

'Z' represents an optionally substituted single or fused group selected from aryl, heterocyclyl or cycloalkyl groups;

In a preferred embodiment, 'Z' is selected from optionally substituted aryl or heterocyclyl groups;

In a further preferred embodiment, the aryl group may be selected from substituted or unsubstituted monocyclic or bicyclic aromatic groups;

In a still further preferred embodiment, the aryl group is an optionally substituted phenyl group.

When 'Z' represents a heterocyclyl group, the heterocyclyl group may be selected from single or fused mono or bi cyclic aromatic groups containing one or more hetero atoms selected from O, N or S;

In a still preferred embodiment, when 'Z' represents heteroaromatic group, the heteroaromatic group may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl groups.

'X' represents either a bond, or may be selected from O, S(O)$_o$ or NR$_4$; wherein R$_4$ is as defined earlier;

'W' represents substituted or unsubstituted linear or branched ($C_1$-$C_6$)alkyl, ($C_2$-$C_6$)alkenyl groups;

R$_1$ represents hydrogen, optionally substituted, ($C_1$-$C_6$) alkyl, ($C_3$-$C_6$)cycloalkyl, alkoxyalkyl, hydroxyalkyl, aminoalkyl, aryl, heterocyclyl, aralkyl, heterocyclylalkyl groups;

R$_2$ represents hydrogen, or the groups selected from ($C_1$-$C_6$)alkyl, aryl, heterocyclyl, aralkyl, heterocyclylalkyl, ($C_1$-$C_6$)alkoxy, hydroxyalkyl, thio($C_1$-$C_6$)alkyl, amino, aminoalkyl, alkylamino, each of which may be optionally substituted;

Alternatively R$_1$ and R$_2$ wherever possible, together may form 4 to 7 membered saturated or partially saturated ring containing from 0-2 additional heteroatoms selected from the group consisting of N, O, and S(O)$_o$;

R$_3$ at each occurrence independently represents hydrogen, halogen, ($C_1$-$C_3$)alkyl, halo($C_1$-$C_3$)alkyl, ($C_1$-$C_3$)alkoxy, thio ($C_1$-$C_3$)alkyl, sulfenyl derivatives, sulfonyl derivatives;

'n' represents integers from 0-3;

When A, R$_1$, R$_2$, R$_3$ or R$_4$ are substituted, the substituents at each occurrence may be independently selected from hydroxyl, oxo, halo, thiol, nitro, amino, cyano, formyl, or substituted or unsubstituted groups selected from amidino, alkyl, haloalkyl, perhaloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heterocyclylalkyl, heterocycloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, cycloalkylthio, arylthio, heterocyclylthio, alkylsulfinyl, cycloalkylsulfinyl, arylsulfinyl, heterocyclylsulfinyl, alkylsulfonyl, cycloalkylsulfonyl, arylsulfonyl, heterocyclylsulfonyl, alkylsulfonylamino, cycloalkylsulfonylamino, arylsulfonylamino, heterocyclylsulfonylamino, alkylsulfonyloxy, cycloalkylsulfonyloxy, arylsulfonyloxy, heterocyclylsulfonyloxy, alkoxycarbonylamino, aryloxycarbonylamino, aralkyloxycarbonylamino, aminocarbonylamino, alkylaminocarbonylamino, alkoxyamino, hydroxylamino, sulfenyl derivatives, sulfonyl derivatives, sulfonic acid and its derivatives.

When the substituents on A, $R_1$, $R_2$, $R_3$ or $R_4$ are further substituted, the substituents may be selected from one or more groups described above.

The various groups, radicals and substituents used anywhere in the specification are described in the following paragraphs. In a further preferred embodiment the groups, radicals described above may be selected from:

- the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;
- the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains;
- the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like;
- the "cycloalkenyl" group used either alone or in combination with other radicals, are preferably selected from cyclopropenyl, 1-cyclobutenyl, 2-cylobutenyl, 1-cyclopentenyl, 2-cyclopentenyl, 3-cyclopentenyl, 1-cyclohexenyl, 2-cyclohexenyl, 3-cyclohexenyl and the like; The terms "bicycloalkenyl" means more than one cycloalkenyl groups fused together;
- the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;
- the "cycloalkoxy" group used either alone or in combination with other radicals, is selected from a cyclic radical containing three to seven carbons, more preferably cyclopropyloxy, cyclobutylxoy, cyclopentyloxy, cyclohexyloxy and the like; The terms "bicycloalkyloxy" means more than one cycloalkyl groups fused together;
- the "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like;
- the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;
- the "haloalkoxy" group is selected from suitable haloalkyl, as defined above, directly attached to an oxygen atom, more preferably groups selected from fluoromethoxy, chloromethoxy, fluoroethoxy, chloroethoxy and the like;
- the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;
- the "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like;
- the "heterocyclyl" or "heterocyclic" group used either alone or in combination with other radicals, is selected from suitable aromatic or non-aromatic radicals containing one or more hetero atoms selected from O, N or S. The non-aromatic radicals may be saturated, partially saturated or unsaturated mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl, and the like; the aromatic radicals, may be selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;
- the groups "heterocycloxy", "heterocylylalkoxy" are selected from suitable heterocyclyl, heterocylylalkyl groups respectively, as defined above, attached to an oxygen atom;
- the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;
- the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;
- the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted;

the "mono-substituted amino" group used either alone or in combination with other radicals, represents an amino group substituted with one group selected from ($C_1$-$C_6$) alkyl, substituted alkyl, aryl, substituted aryl or arylalkyl groups as defined earlier, more preferably such groups are selected from methylamine, ethylamine, n-propylamine, n-butylamine, n-pentylamine and the like;

the 'disubstituted amino" group used either alone or in combination with other radicals, represents an amino group, substituted with two radicals that may be same or different selected from ($C_1$-$C_6$)alkyl, substituted alkyl, aryl, substituted aryl, or arylalkyl groups, as defined above, more preferably the groups are selected from dimethylamino, methylethylamino, diethylamino, phenylmethyl amino and the like;

the "arylamine" used either alone or in combination with other radicals, represents an aryl group, as defined above, linked through amino having a free valence bond from the nitrogen atom, more preferably the groups are selected from phenylamino, naphthylamino, N-methyl anilino and the like;

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N$—C=O), wherein the amino group is mono- or di-substituted or unsubstituted, more preferably the groups are selected from methyl amide, dimethyl amide, ethyl amide, diethyl amide, and the like;

the "aminocarbonyl" group used either alone or in combination with other radicals, may be selected from 'aminocarbonyl', 'aminocarbonylalkyl", "n-alkylaminocarbonyl", "N-arylaminocarbonyl", "N,N-dialkylaminocarbonyl", "N-alkyl-N-arylaminocarbonyl", and "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote amiocarbonyl radicals substituted, respectively, with one aryl radical, or one alkyl, and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "arylthio" group used either alone or in combination with other radicals, denotes a comprising an aryl group as defined above, linked through a divalent sulfur atom having a free valence bond from the sulfur atom, more preferably the groups may be selected from phenylthio, naphthylthio, tetrahydronaphthylthio, indanethio, biphenylthio, and the like;

the "heterocyclylthio" group used either alone or in combination with other radicals, denotes a comprising an heterocyclyl group as defined above, linked through a divalent sulfur atom having a free valence bond from the sulfur atom, more preferably the groups may be selected from aziridinylthio, azetidinylthio, pyrrolidinylthio, imidazolidinylthio, piperidinylthio, piperazinylthio, 2-oxopiperidinylthio, 4-oxopiperidinylthio, 2-oxopiperazinylthio, 3-oxopiperazinylthio, morpholinylthio, thiomorpholinylthio, 2-oxomorpholinylthio, azepinylthio, diazepinylthio, oxapinylthio, thiazepinylthio, oxazolidinylthio, thiazolidinylthio, dihydrothiophenethio, dihydropyranthio, dihydrofuranthio, dihydrothiazolethio, benzopyranylthio, benzopyranonylthio, benzodihydrofuranylthio, benzodihydrothienylthio, pyrazolopyrimidonylthio, azaquinazolinoylthio, thienopyrimidonylthio, quinazolonylthio, pyrimidonylthio, benzoxazinylthio, benzoxazinonylthio, benzothiazinylthio, benzothiazinonylthio, thieno piperidinylthio, pyridylthio, thienylthio, furylthio, pyrrolylthio, oxazolylthio, thiazolylthio, isothiazolylthio, imidazolylthio, isoxazolylthio, oxadiazolylthio, thiadiazolylthio, triazolylthio, tetrazolylthio, benzofuranylthio, benzothienylthio, indolinylthio, indolylthio, azaindolylthio, azaindolinylthio, pyrazolopyrimidinylthio, azaquinazolinylthio, pyridofuranylthio, pyridothienylthio, thienopyrimidylthio, quinolinylthio, pyrimidinylthio, pyrazolylthio, quinazolinylthio, pyridazinylthio, triazinylthio, benzimidazolylthio, benzotriazolylthio, phthalazynilthio, naphthylidinylthio, purinylthio, carbazolylthio, phenothiazinylthio, phenoxazinylthio, benzoxazolylthio, benzothiazolylthio and the like;

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonylamino", "alkylaminocarbonylamino", "dialkylaminocarbonylamino" groups used alone or in combination with other radicals, is a carbonylamino (—CONH$_2$) group, attached to amino(NH$_2$), alkylamino group or dialkylamino group respectively, where alkyl group is as defined above;

the "amidino" group used either alone or in combination with other radicals, represents a —C(=NH)—NH$_2$ radical; the "alkylamidino" group represents an alkyl radical, as described above, attached to an amidino group;

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group, —SO— or R$_x$SO, where R$_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —SO$_2$—, or R$_x$SO$_2$—, where R$_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like. The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits.

Preferably, the patient is a human.

Suitable groups and substituents on the groups may be selected from those described anywhere in the specification.

Particularly useful compounds may be selected from

N-((tetrahydro-2H-pyran-4-yl)methyl)-2-(4-(1-(((4-(trifluoromethyl)benzyl)oxy)imino)propyl)phenoxy)acetamide;

N-((tetrahydro-2H-pyran-4-yl)methyl)-2-((5-(1-(((4-(trifluoromethyl) benzyl)oxy)imino)ethyl)pyridin-2-yl)oxy)acetamide;

N-((tetrahydro-2H-pyran-4-yl)methyl)-2-((5-(1-(((4-(trifluoromethyl) benzyl)oxy)imino)ethyl)pyridin-2-yl)amino)acetamide;

N-((tetrahydro-2H-pyran-4-yl)methyl)-2-((4-(1-(((4-(trifluoromethyl)benzyl)oxy)imino)propyl)phenyl)amino)acetamide;

2,2'-((5-(1-(((4-(trifluoromethyl)benzyl)oxy)imino)ethyl)oxazol-2-yl)azanediyl)bis(N-((tetrahydro-2H-pyran-4-yl)methyl)acetamide);

N-((tetrahydro-2H-pyran-4-yl)methyl)-2-((1-(4-(trifluoromethyl)benzyl)-3-(((((4-(trifluoromethyl)benzyl)oxy)imino)methyl)-1H-indol-5-yl)oxy)acetamide;

2-(2-methyl-4-(2-phenyl-1-(((4-(trifluoromethyl)benzyl)oxy)imino)ethyl)phenoxy)-N-((tetrahydro-2H-pyran-4-yl)methyl)acetamide;

2-(4-(2-phenyl-1-(((4-(trifluoromethyl)benzyl)oxy)imino)ethyl)phenoxy)-N-((tetrahydro-2H-pyran-4-yl)methyl)acetamide;

2-(4-(2-phenyl-1-(((3-(trifluoromethyl)benzyl)oxy)imino)ethyl)phenoxy)-N-((tetrahydro-2H-pyran-4-yl)methyl)acetamide;

2-(4-(2-(pyridin-4-yl)-1-(((4-(trifluoromethyl)benzyl)oxy)imino)ethyl)phenoxy)-N-((tetrahydro-2H-pyran-4-yl)methyl)acetamide;

2-(4-(2-morpholino-1-(((4-(trifluoromethyl)benzyl)oxy)imino)ethyl)phenoxy)-N-((tetrahydro-2H-pyran-4-yl)methyl)acetamide;

N-((tetrahydro-2H-pyran-4-yl)methyl)-2-(4-(2-thiomorpholino-1-(((4-(trifluoromethyl) benzyl)oxy)imino)ethyl)phenoxy)acetamide;

2-(2-methyl-4-(2-(thiophen-3-yl)-1-(((4-(trifluoromethyl)benzyl)oxy)imino)ethyl)phenoxy)-N-((tetrahydro-2H-pyran-4-yl)methyl)acetamide;

N-((tetrahydro-2H-pyran-4-yl)methyl)-2-(4-((((4-(trifluoromethyl) benzyl)oxy)imino)methyl)phenoxy)acetamide;

N-((tetrahydro-2H-pyran-4-yl)methyl)-2-(4-(1-(((4-(trifluoromethyl)benzyl)oxy)imino)ethyl)phenoxy)acetamide;
N-((tetrahydro-2H-pyran-4-yl)methyl)-2-((5-((((4-(trifluoromethyl) benzyl)oxy)imino)methyl)pyridin-2-yl)oxy)acetamide;
N-((tetrahydro-2H-pyran-4-yl)methyl)-2-((4-(1-(((4-(trifluoromethyl) benzyl)oxy)imino)ethyl)phenyl)amino)acetamide;
2-((5-(1-(((4-cyanobenzyl)oxy)imino)ethyl)pyridin-2-yl)oxy)-N-((tetrahydro-2H-pyran-4-yl)methyl)acetamide;
N-((tetrahydro-2H-pyran-4-yl)methyl)-2-((5-(1-(((4-(trifluoromethyl)benzyl)oxy)imino)propyl)pyridin-2-yl)oxy)acetamide;
N-((tetrahydro-2H-pyran-4-yl)methyl)-2-((5-(1-(((4-(trifluoromethyl)benzyl)oxy)imino)propyl)pyridin-2-yl)amino)acetamide;
2-((5-(1-((benzyloxy)imino)propyl)pyridin-2-yl)oxy)-N-((tetrahydro-2H-pyran-4-yl)methyl)acetamide;
2-((5-(1-(((4-methylbenzyl)oxy)imino)propyl)pyridin-2-yl)oxy)-N-((tetrahydro-2H-pyran-4-yl)methyl)acetamide;
2-((5-(1-(((4-methoxybenzyl)oxy)imino)propyl)pyridin-2-yl)oxy)-N-((tetrahydro-2H-pyran-4-yl)methyl)acetamide;
2-((5-(1-(((4-fluorobenzyl)oxy)imino)propyl)pyridin-2-yl)oxy)-N-((tetrahydro-2H-pyran-4-yl)methyl)acetamide;
2-((5-(1-(((4-cyanobenzyl)oxy)imino)propyl)pyridin-2-yl)oxy)-N-((tetrahydro-2H-pyran-4-yl)methyl)acetamide;
2-(2-methyl-4-(1-(((4-(trifluoromethyl)benzyl)oxy)imino)butyl)phenoxy)-N-((tetrahydro-2H-pyran-4-yl)methyl)acetamide;
2-(4-(2-methoxy-1-(((4-(trifluoromethyl)benzyl)oxy)imino)ethyl)phenoxy)-N-((tetrahydro-2H-pyran-4-yl)methyl)acetamide;
2-(4-(2-hydroxy-1-(((4-(trifluoromethyl)benzyl)oxy)imino)ethyl)phenoxy)-N-((tetrahydro-2H-pyran-4-yl)methyl)acetamide;
2-(2-methyl-4-(1-(((4-methylbenzyl)oxy)imino)-2-phenylethyl)phenoxy)-N-((tetrahydro-2H-pyran-4-yl)methyl)acetamide;
2-(4-(1-(((4-methylbenzyl)oxy)imino)-2-phenylethyl)phenoxy)-N-((tetrahydro-2H-pyran-4-yl)methyl)acetamide;
2-(4-(1-(((4-fluorobenzyl)oxy)imino)-2-phenylethyl)-2-methylphenoxy)-N-((tetrahydro-2H-pyran-4-yl)methyl)acetamide;
2-(4-(1-(((4-fluorobenzyl)oxy)imino)-2-phenylethyl)phenoxy)-N-((tetrahydro-2H-pyran-4-yl)methyl)acetamide;
2-(4-(1-(((4-chlorobenzyl)oxy)imino)-2-phenylethyl)-2-methylphenoxy)-N-((tetrahydro-2H-pyran-4-yl)methyl)acetamide;
2-(4-(1-(((4-chlorobenzyl)oxy)imino)-2-phenylethyl)phenoxy)-N-((tetrahydro-2H-pyran-4-yl)methyl)acetamide;
2-(2-methyl-4-(2-phenyl-1-(((4-(trifluoromethoxy)benzyl)oxy)imino)ethyl)phenoxy)-N-((tetrahydro-2H-pyran-4-yl)methyl)acetamide;
2-(4-(2-phenyl-1-(((4-(trifluoromethoxy)benzyl)oxy)imino)ethyl)phenoxy)-N-((tetrahydro-2H-pyran-4-yl)methyl)acetamide;
2-(4-(1-(((4-methoxybenzyl)oxy)imino)-2-phenylethyl)-2-methylphenoxy)-N-((tetrahydro-2H-pyran-4-yl)methyl)acetamide.
2-(4-(1-(((4-methoxybenzyl)oxy)imino)-2-phenylethyl)phenoxy)-N-((tetrahydro-2H-pyran-4-yl)methyl)acetamide;
2-(4-(1-(((4-(methylsulfonyl)benzyl)oxy)imino)propyl)phenoxy)-N-((tetrahydro-2H-pyran-4-yl)methyl)acetamide;
2-(4-(2-phenyl-1-((pyridin-2-ylmethoxy)imino)ethyl)phenoxy)-N-((tetrahydro-2H-pyran-4-yl)methyl)acetamide;
2-(4-(1-((2-(1H-indol-1-yl)ethoxy)imino)propyl)phenoxy)-N-((tetrahydro-2H-pyran-4-yl)methyl)acetamide;
2-(4-(1-(((5-ethylpyrimidin-2-yl)oxy)imino)propyl)phenoxy)-N-((tetrahydro-2H-pyran-4-yl)methyl)acetamide;
2-(4-(1-(((5-methyl-2-phenyloxazol-4-yl)methoxy)imino)propyl)phenoxy)-N-((tetrahydro-2H-pyran-4-yl)methyl)acetamide;
2-(4-(1-(((3-(tert-butyl)-1-(p-tolyl)-1H-pyrazol-5-yl)methoxy)imino)propyl)phenoxy)-N-((tetrahydro-2H-pyran-4-yl)methyl)acetamide;
N-((tetrahydro-2H-pyran-4-yl)methyl)-2-((5-(((4-(trifluoromethyl)benzyl)oxy)imino)-5,6,7,8-tetrahydronaphthalen-2-yl)oxy)acetamide;
2-((5-(((4-chlorobenzyl)oxy)imino)-5,6,7,8-tetrahydronaphthalen-2-yl)oxy)-N-((tetrahydro-2H-pyran-4-yl)methyl)acetamide;
2-((5-(((4-cyanobenzyl)oxy)imino)-5,6,7,8-tetrahydronaphthalen-2-yl)oxy)-N-((tetrahydro-2H-pyran-4-yl)methyl)acetamide;
2-((5-(((4-methoxybenzyl)oxy)imino)-5,6,7,8-tetrahydronaphthalen-2-yl)oxy)-N-((tetrahydro-2H-pyran-4-yl)methyl)acetamide;
Methyl 3-((((6-(2-oxo-2-(((tetrahydro-2H-pyran-4-yl)methyl)amino)ethoxy)-3,4-dihydronaphthalen-1(2H)-ylidene)amino)oxy)methyl)benzoate;
N-((tetrahydro-2H-pyran-4-yl)methyl)-2-((5-(1-(((4-(trifluoromethyl)benzyl)oxy)imino)ethyl)quinolin-8-yl)oxy)acetamide;
2-methyl-N-((tetrahydro-2H-pyran-4-yl)methyl)-2-(4-(1-(((4-(trifluoromethyl)benzyl)oxy)imino)propyl)phenoxy)propanamide;
2-methyl-N-((tetrahydro-2H-pyran-4-yl)methyl)-2-(4-(1-(((4-(trifluoromethyl)benzyl)oxy)imino)ethyl)phenoxy)propanamide;
2-(4-(1-(((tetrahydro-2H-pyran-4-yl)methoxy)imino)ethyl)phenoxy)-N-((tetrahydro-2H-pyran-4-yl)methyl)acetamide;
2-(4-(1-((cyclohexylmethoxy)imino)ethyl)phenoxy)-N-((tetrahydro-2H-pyran-4-yl)methyl)acetamide;
2-(4-(1-((naphthalen-2-ylmethoxy)imino)ethyl)phenoxy)-N-((tetrahydro-2H-pyran-4-yl)methyl)acetamide;
2-((5-(2-phenyl-1-(((4-(trifluoromethyl)benzyl)oxy)imino)ethyl)pyridin-2-yl)oxy)-N-((tetrahydro-2H-pyran-4-yl)methyl)acetamide;
2-((5-(2-phenyl-1-(((4-(trifluoromethyl)benzyl)oxy)imino)ethyl)pyridin-2-yl)amino)-N-((tetrahydro-2H-pyran-4-yl)methyl)acetamide;
N-((tetrahydro-2H-pyran-4-yl)methyl)-2-((3-((((4-(trifluoromethyl)benzyl)oxy)imino)methyl)-1H-indol-5-yl)oxy)acetamide;
N-((tetrahydro-2H-pyran-4-yl)methyl)-2-((3-(1-(((4-(trifluoromethyl)benzyl)oxy)imino)ethyl)-1H-indol-5-yl)oxy)acetamide;
N-((tetrahydro-2H-pyran-4-yl)methyl)-2-((3-(1-(((4-(trifluoromethyl)benzyl)oxy)imino)propyl)-1H-indol-5-yl)oxy)acetamide;
2-((3-(2-phenyl-1-(((4-(trifluoromethyl)benzyl)oxy)imino)ethyl)-1H-indol-5-yl)oxy)-N-((tetrahydro-2H-pyran-4-yl)methyl)acetamide;
N-((tetrahydro-2H-pyran-4-yl)methyl)-3-(5-(1-(((4-(trifluoromethyl)benzyl)oxy)imino)ethyl)pyrimidin-2-yl)propanamide;
N 4(tetrahydro-2H-pyran-4-yl)methyl)-3-(5-(1-(((4-(trifluoromethyl)benzyl)oxy)imino)propyl)pyrimidin-2-yl)propanamide;
3-(5-(2-phenyl-1-(((4-(trifluoromethyl)benzyl)oxy)imino)ethyl)pyrimidin-2-yl)-N-((tetrahydro-2H-pyran-4-yl)methyl)propanamide;

N-((tetrahydro-2H-pyran-4-yl)methyl)-2-((5-(1-(((4-(trifluoromethyl)benzyl)oxy)imino)propyl)quinolin-8-yl)oxy)acetamide;

2-((5-(2-phenyl-1-(((4-(trifluoromethyl)benzyl)oxy)imino)ethyl)quinolin-8-yl)oxy)-N-((tetrahydro-2H-pyran-4-yl)methyl)acetamide;

The present invention also discloses certain novel intermediates suitable for the preparation of compounds of formula (I). Specifically, the present invention discloses 2-((5-(14((4-(trifluoromethyl)benzyl)oxy)imino)ethyl)pyridin-2-yl)oxy)acetic acid;

2,2'-((5-(1-(((4-(trifluoromethyl)benzyl)oxy)imino)ethyl)oxazol-2-yl)azanediyl)diacetic acid;

2-((1-(4-(trifluoromethyl)benzyl)-3-((((4-(trifluoromethyl)benzyl)oxy)imino)methyl)-1H-indol-5-yl)oxy)acetic acid;

2-((5-(1-(((4-(trifluoromethyl)benzyl)oxy)imino)ethyl)quinolin-8-yl)oxy)acetic acid;

2-((5-(1-(((4-(trifluoromethyl)benzyl)oxy)imino)ethyl)pyridin-2-yl)amino)acetic acid;

2-((5-((((4-(trifluoromethyl)benzyl)oxy)imino)methyl)pyridin-2-yl)oxy)acetic acid;

2-((5-(1-(((4-cyanobenzyl)oxy)imino)ethyl)pyridin-2-yl)oxy)acetic acid;

2-((5-(1-(((4-(trifluoromethyl)benzyl)oxy)imino)propyl)pyridin-2-yl)oxy)acetic acid;

2-((5-(1-(((4-(trifluoromethyl)benzyl)oxy)imino)propyl)pyridin-2-yl)amino)acetic acid;

2-((5-(1-((benzyloxy)imino)propyl)pyridin-2-yl)oxy)acetic acid;

2-((5-(1-(((4-methylbenzyl)oxy)imino)propyl)pyridin-2-yl)oxy)acetic acid;

2-((5-(1-(((4-methoxybenzyl)oxy)imino)propyl)pyridin-2-yl)oxy)acetic acid;

2-((5-(1-(((4-fluorobenzyl)oxy)imino)propyl)pyridin-2-yl)oxy)acetic acid;

2-((5-(1-(((4-cyanobenzyl)oxy)imino)propyl)pyridin-2-yl)oxy)acetic acid;

2-((5-(2-phenyl-1-(((4-(trifluoromethyl)benzyl)oxy)imino)ethyl)pyridin-2-yl)oxy)acetic acid;

2-((5-(2-phenyl-1-(((4-(trifluoromethyl)benzyl)oxy)imino)ethyl)pyridin-2-yl)amino)acetic acid;

2-((3-((((4-(trifluoromethyl)benzyl)oxy)imino)methyl)-1H-indol-5-yl)oxy)acetic acid;

2-((3-(1-(((4-(trifluoromethyl)benzyl)oxy)imino)ethyl)-1H-indol-5-yl)oxy)acetic acid;

2-((3-(1-(((4-(trifluoromethyl)benzyl)oxy)imino)propyl)-1H-indol-5-yl)oxy)acetic acid;

2-((3-(2-phenyl-1-(((4-(trifluoromethyl)benzyl)oxy)imino)ethyl)-1H-indol-5-yl)oxy)acetic acid;

3-(5-(1-(((4-(trifluoromethyl)benzyl)oxy)imino)ethyl)pyrimidin-2-yl)propanoic acid;

3-(5-(1-(((4-(trifluoromethyl)benzyl)oxy)imino)propyl)pyrimidin-2-yl)propanoic acid;

3-(5-(2-phenyl-1-(((4-(trifluoromethyl)benzyl)oxy)imino)ethyl)pyrimidin-2-yl)propanoic acid;

2-((5-(1-(((4-(trifluoromethyl)benzyl)oxy)imino)propyl)quinolin-8-yl)oxy)acetic acid;

2-((5-(2-phenyl-1-(((4-(trifluoromethyl)benzyl)oxy)imino)ethyl)quinolin-8-yl)oxy)acetic acid.

The novel compounds of this invention may be prepared using the reactions and techniques as shown in scheme below and described in this section. The reactions are performed in solvents appropriate to the reagents and materials employed and are suitable for the transformations being affected. It is understood by those skilled in the art that the nature and order of the synthetic steps presented may be varied for the purpose of optimizing the formation of the compounds of the present invention. It will also be well appreciated that one or more of the reactants may be protected and deprotected for facile synthesis by techniques known to persons skilled in the art. It will also be appreciated that one or more of the compounds of the present invention may exist in stereoisomeric and/or diastereomeric forms. Such stereoisomers and/or diastereoisomers as well as their optical antipodes are to be construed to be within the scope of the present invention. It will also be well appreciated that one or more of these compounds may be converted to their salts and other derivatives based on the specific groups present on the compounds, which can be well comprehended by persons skilled in the art. Such salts and/or other derivatives, as the case may be should also be construed to be within the scope of the present invention.

Scheme: 1 The compounds of general formula (I) wherein all the symbols are as defined earlier, may be prepared by reactions outlined in Scheme 1 below which comprises:

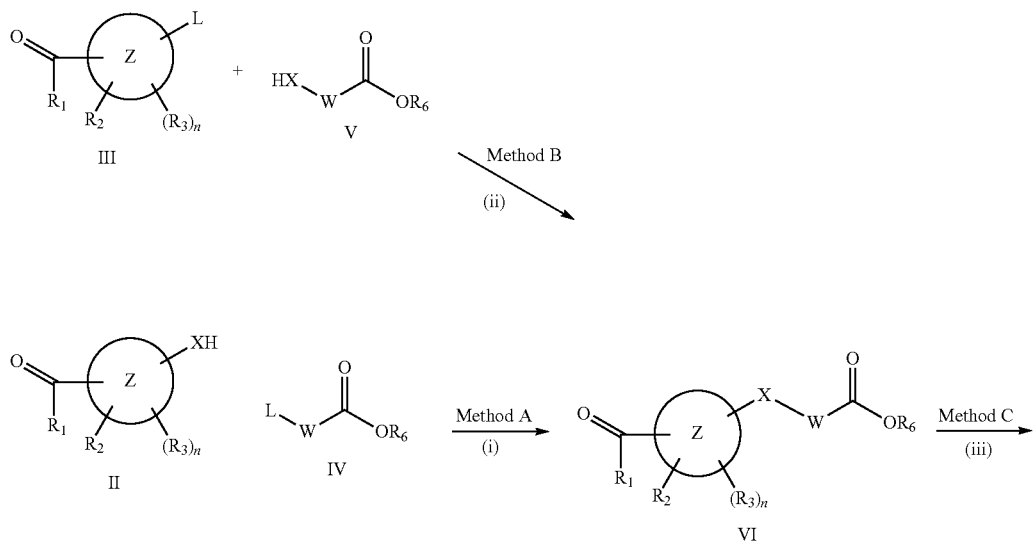

-continued

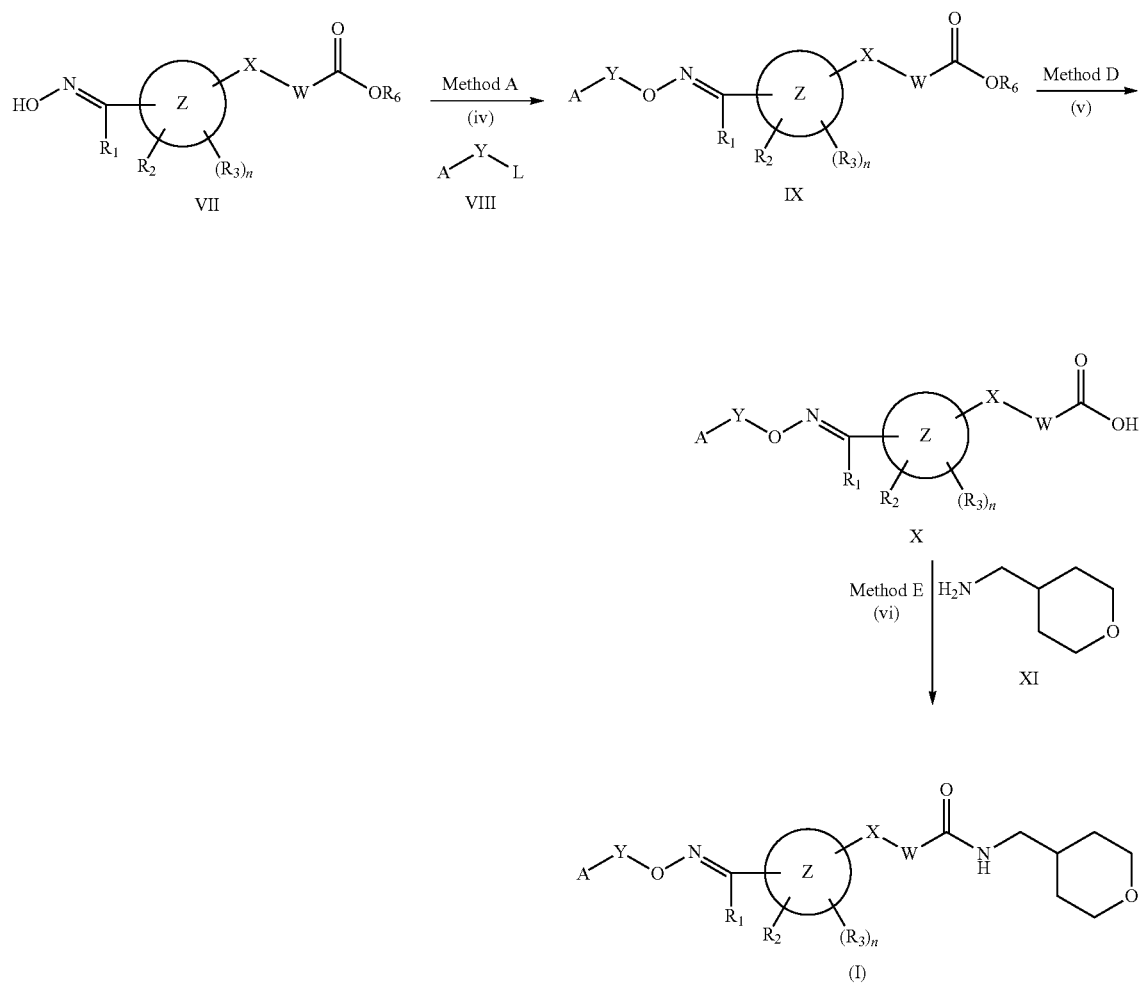

i. Compounds of general formula VI wherein $R_6$ represents $C_1$—$C_6$ linear or branched alkyl or aralkyl, and all other symbols are as defined earlier may be prepared by coupling of compounds of general formula II wherein all the symbols are as defined earlier and compounds of general formula IV whereas 'L' represents a suitable leaving group and all other symbols are as defined earlier using suitable base and suitable reaction medium by means of the methods available in the literature for standard neucleophilic substitution reaction;

ii. Alternatively compounds of general formula VI wherein all the symbols are as defined earlier may be prepared by coupling of compounds of formula III whereas all the symbols are as defined earlier and compounds of general formula V wherein all other symbols are as defined using suitable base and suitable reaction medium by means of the methods available in the literature for standard neucleophilic substitution reaction;

iii. Compounds of general formula VII wherein all the symbols are as defined earlier may be prepared by reacting compounds of general formula VI wherein all the symbols are as defined earlier with hydroxylamine hydrochloride in presence of suitable base and suitable solvents;

iv. Compounds of formula IX wherein all the symbols are as defined earlier may be prepared by coupling of compounds of formula VII wherein all the symbols are as defined earlier and compounds of general formula VIII where 'L' represents a suitable leaving group and all other symbols are as defined earlier using suitable base and suitable reaction medium;

v. Compounds of general formula X wherein all the symbols are as defined earlier may be prepared by hydrolysis of compounds of general formula IX wherein all the symbols are as defined earlier under suitable condition;

vi. Compounds of formula (I) wherein all the symbols are as defined earlier may be prepared by coupling of compounds of formula X wherein all symbols are as defined earlier and (tetrahydro-2H-pyran-4-yl)methanamine (XI) wherein all symbols are as defined using suitable methods available in the literature for standard peptide coupling;

Scheme: 2 Alternatively the compounds of general formula (I) wherein all the symbols are as defined earlier, may be prepared by reactions outlined in Scheme 2 below which comprises:

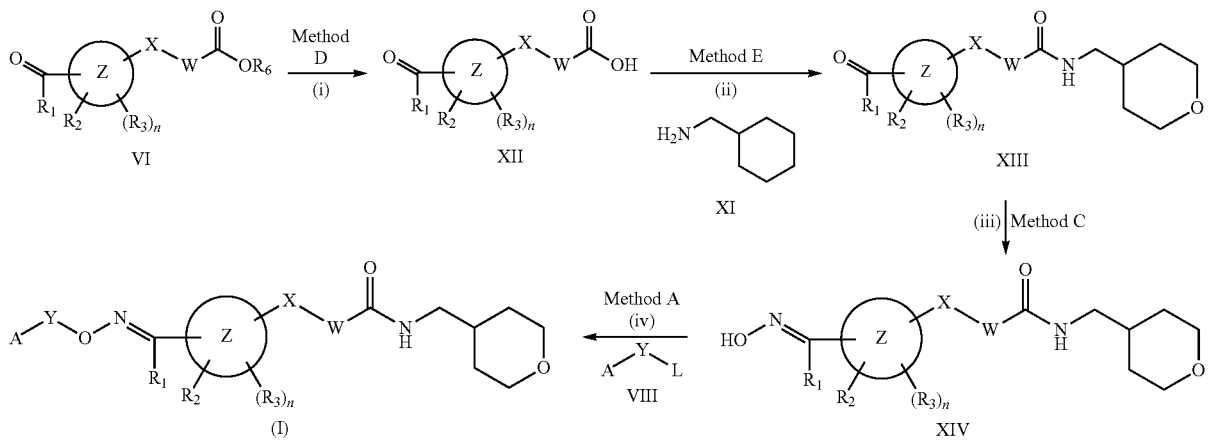

i. Compounds of general formula XII wherein all the symbols are as defined earlier may be prepared by the hydrolysis of compounds of general formula VI wherein all the symbols are as defined earlier under suitable condition;
ii. Compounds of formula XIII wherein all the symbols are as defined earlier may be prepared by coupling of compounds of formula XII wherein all symbols are as defined earlier and (tetrahydro-2H-pyran-4-yl)methanamine (XI) wherein all symbols are as defined earlier using suitable methods available in the literature for standard peptide coupling;
iii. Compounds of general formula XIV wherein all the symbols are as defined earlier may be prepared by reacting compounds of general formula XIII wherein all the symbols are as defined earlier with hydroxylamine hydrochloride in presence of suitable base and suitable solvents;
iv. Compounds of formula (I) wherein all the symbols are as defined earlier may be prepared by coupling of compounds of formula XIV wherein all the symbols are as defined earlier and compounds of general formula VIII wherein all the symbols are as defined earlier using suitable base and suitable reaction medium.

Method A: The compounds of formula VI, IX and (I) wherein all the symbols are as defined earlier may be prepared by appropriate starting materials as described in Scheme 1 and Scheme 2 using suitable inorganic base(s) such as NaOH, KOH, $K_2CO_3$, $Cs_2CO_3$ and the like or organic base(s) such as pyridine, triethyl amine, diisopropyl ethylamine and the like. The reaction may be carried out neat or in presence of suitable protic solvent(s) such as methanol, ethanol, butanol and the like or suitable aprotic solvent(s) such as dimethyl formamide, tetrahydrofuran, dichloromethane and the like or suitable mixtures thereof. The reaction may be carried out at a temperature in the range 0° C. to reflux temperature of the solvent(s) used and the reaction time may range from 1 to 48 hours.

Method B: The compounds of formula VI wherein all the symbols are as defined earlier may be prepared by using appropriate starting materials as described in Scheme 1 using suitable inorganic base(s) such as NaOH, KOH, $K_2CO_3$, $Cs_2CO_3$ and the like or suitable organic base(s) such as pyridine, triethyl amine, diisopropyl ethylamine and the like. Alternatively the compounds of formula VI wherein all the symbols are as defined earlier may also be prepared by using suitable palladium based catalyst such as palladium acetate, $Pd(Ph_3P)_4$ and the like and with or without organic ligand such as BINAP and the like. The reaction may be carried out neat or in presence of suitable protic solvent(s) such as methanol, ethanol, butanol and the like or suitable aprotic solvent(s) such as dimethyl formamide, toluene, tetrahydrofuran, dichloromethane and the like or mixtures thereof. The reaction may be carried out at a temperature in the range 0° C. to reflux temperature of the solvent(s) used and the reaction time may range from 1 to 48 hours.

Method C: The compounds of the formula VII and XIV wherein all the symbols are as defined earlier may be prepared by reacting appropriate ketones as described in Scheme 1 and Scheme 2 with hydroxylamine hydrochloride in the presence of a base(s) like NaOH, NaOAc, pyridine and the like. The reaction may be carried out in presence of suitable solvent(s) such as methanol, ethanol, butanol, water and the like or suitable mixtures thereof. The reaction may be carried out at a temperature in the range 0° C. to reflux temperature of the solvent(s) used and the reaction time may range from 1 to 48 hours.

Method D: The compounds of the formula X and XII wherein all the symbols are as defined earlier may be prepared by hydrolyzing appropriate esters as described in Scheme 1 and Scheme 2 using suitable base(s) e.g., NaOH, LiOH, KOH and the like. Reaction may be conducted in suitable solvent(s) such as methanol, ethanol, THF, water and the like or the mixtures thereof. The reaction may be carried out at a temperature in the range 20° C. to reflux temperature of the solvent(s) used and the reaction time may range from 1 to 48 hours.

Method E: The compounds of the formula (I) and XIII wherein all the symbols are as defined earlier may be prepared by coupling reaction of appropriate acid and appropriate amine as described in scheme 1 and scheme 2 under suitable conditions such as those described in *Tetrahedron*, 2005, 61(46), 10827-10852 with suitable modifications and alterations as are well known to a skilled person. The reaction may be carried out in presence of reagents(s) such as N-(3-dimethylaminopropyl)-N'-ethylcarbodimide hydrochloride (EDCl) & 1-Hydroxybenzotriazole (HOBT), and the like. The reaction may be carried in suitable solvent(s) such as dimethyl formamide, tetrahydrofuran, dichloromethane and the like or mixtures thereof.

The reaction may be carried out at a temperature in the range 0° C. to reflux temperature of the solvent(s) used and the reaction time may range from 1 to 48 hours.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The invention is explained in greater detail by the examples given below, which are provided by way of illustration only and therefore should not be construed to limit the scope of the invention.

1H NMR spectral data given in the examples (vide infra) are recorded using a 400 MHz spectrometer (Bruker AVANCE-400) and reported in δ scale. Until and otherwise mentioned the solvent used for NMR is $CDCl_3$ using tetramethyl silane as the internal standard.

Example 1

N-((tetrahydro-2H-pyran-4-yl)methyl)-2-(4-(1-(((4-(trifluoromethyl)benzyl)oxy)imino)propyl)phenoxy)acetamide Step 1: Ethyl 2-(4-propionylphenoxy)acetate To a solution of 1-(4-hydroxyphenyl)propan-1-one (33 g, 0.2200 moles) in DMF (165 mL), potassium carbonate (60.7 gm, 0.4400 moles) and ethyl bromo acetate (40.6 gm, 0.2420 moles) were added and the reaction mixture was srirred at 50° C. for 3 hours. The reaction mixture was poured into ice cold water and extracted with ethyl acetate. The combined ethyl acetate extract was washed with water & brine, dried over sodium sulphate and evaporated under reduced pressure to yield 49 gm (94%) of product as thick liquid.

$^1$H NMR: DMSO-$d_6$ δ 1.06 (t, J=7.2 Hz, 3H), 1.20 (t, J=4.8 Hz, 3H), 2.96 (q, J=7.4 Hz, 2H), 4.14 (q, J=3.6 Hz, 2H), 4.88 (s, 2H), 7.02 (dd, J=2.0 & 6.8 Hz, 2H), 7.92 (dd, J=2.0 & 6.8 Hz, 2H).

Step 2: Ethyl 2-(4-(1-(hydroxyimino)propyl)phenoxy)acetate

To a solution of the product of step 1 (49 g, 0.2076 moles) in methanol (343 ml), hydroxylamine hydrochloride (28.6 g, 0.4152 moles) and a solution of sodium acetate (34 g, 0.4152 moles) in water (147 ml) were added and the reaction mixture was refluxed for 1 hour. The solvents were evaporated under reduced pressure. The residue was dissolved in water and extracted with ethyl acetate. The combined ethyl acetate extract was washed with water & brine, dried over sodium sulphate and evapourated under reduced pressure to yield 40 gm (76%) of product as solid.

$^1$H NMR: DMSO-$d_6$ δ 1.01 (t, J=7.4 Hz, 3H), 1.21 (t, J=7.0 Hz, 3H), 2.66 (q, J=7.6 Hz, 2H), 4.16 (q, J=7.2 Hz, 2H), 4.79 (s, 2H), 6.93 (dd, J=5.2 & 2.8 Hz, 2H), 7.56 (dd, J=6.8 & 2.0 Hz, 2H), 10.93 (s, 1H).

Step 3: Ethyl 2-(4-(1-(((4-(trifluoromethyl)benzyl)oxy)imino)propyl)phenoxy)acetate To a solution of the product of step 2 (18 g, 0.0723 moles) in DMF (54 mL), cesium carbonate (47 gm, 0.1446 moles) and 4-(trifluoromethyl)benzyl bromide (19 gm, 0.0795 moles) were added and the reaction mixture was srirred at 25° C. for 3 hours. The reaction mixture was poured into ice cold water and extracted with ethyl acetate. The combined ethyl acetate extract was washed with water & brine, dried over sodium sulphate and evapoured under reduced pressure to yield 28 gm (95%) of product as thick liquid.

$^1$H NMR: DMSO-$d_6$ δ 1.05 (t, J=7.4 Hz, 3H), 1.19 (t, J=7.0 Hz, 3H), 2.73 (q, J=7.6 Hz, 2H), 4.16 (q, J=7.2 Hz, 2H), 4.80 (s, 2H), 5.26 (s, 2H), 6.93 (dd, J=7.2 & 2.4 Hz, 2H), 7.56 (dd, J=6.8 & 2.0 Hz, 2H), 7.59 (d, J=8.0 Hz, 2H), 7.72 (d, J=8.0 Hz, 2H)

Step 4: 2-(4-(1-(((4-(trifluoromethyl)benzyl)oxy)imino)propyl)phenoxy)acetic acid To a solution of the product of step 3 (28 g, 0.0683 moles) in THF (140 ml), a solution of lithium hydroxide (4.3 g, 0.1024 moles) in water (140 ml) was added and the reaction mixture was stirred at 25° C. for 3 hours. The solvents were evaporated under reduced pressure. The residue was dissolved in water, acidified with 1N HCl and extracted with ethyl acetate. The combined ethyl acetate extract was washed with water & brine, dried over sodium sulphate and evapourated under reduced pressure to yield 23 gm (88%) of product as solid.

$^1$H NMR: DMSO-$d_6$ δ 1.05 (t, J=7.4 Hz, 3H), 2.73 (q, J=7.4 Hz, 2H), 4.69 (s, 2H), 5.26 (s, 2H), 6.92 (dd, J=2 & 6.8 Hz, 2H), 7.55 (dd, J=2.4 & 7.2 Hz, 2H), 7.59 (d, J=8 Hz, 2H), 7.72 (d, J=8 Hz, 2H).

Step 5: N-((tetrahydro-2H-pyran-4-yl)methyl)-2-(4-(1-(((4-(trifluoromethyl)benzyl)oxy)imino)propyl)phenoxy)acetamide To a solution of the product of step 4 (23 g, 0.0602 moles) in DMF (69 mL), (tetrahydro-2H-pyran-4-yl)methanamine (7.6 gm, 0.0662 moles), HOBT (50 mg, catalytic amount), EDC.HCl (17.5 g, 0.0903 moles) and DMAP (50 mg, catalytic amount) were added and reaction mixture was srirred at 25° C. for 16 hours. The reaction mixture was poured into ice cold water and extracted with ethyl acetate. The combined ethyl acetate extract was washed with water & brine, dried over sodium sulphate and evapourated under reduced pressure. The crude product was purified by coloumn chromatography using ethyl acetate:Hhexane (1:1) as eluent to yield 16.5 g (57%) of product as white solid. $^1$H NMR: DMSO-$d_6$ δ 1.10 (t, J=6.6 Hz, 3H), 1.13-1.16 (m, 2H), 1.46-1.49 (m, 2H), 1.61-1.70 (m, 1H), 2.74 (q, J=7.6 Hz, 2H), 3.01 (t, J=6.6 Hz, 2H), 3.17-3.23 (m, 2H), 3.78-3.81 (dd, J=11.4 & 2.6 Hz, 2H), 4.51 (s, 2H), 5.26 (s, 2H), 6.96 (dd, J=6.8 & 2.0 Hz, 2H), 5.57-5.61 (m, 4H), 7.72 (d, J=8.0 Hz, 2H), 8.10 (t, J=6.0 Hz, NH).

Example 2

2-((5-(1-(((4-(trifluoromethyl)benzyl)oxy)imino)ethyl)pyridin-2-yl)oxy)acetic acid

Step 1: Ethyl 2-((5-acetylpyridin-2-yl)oxy)acetate

To a solution of 1-(6-chloropyridin-3-yl)ethanone (4.0 gm, 0.0257 mole) in DMF (15 mL), cesium carbonate (16.8 gm, 0.051 mole) was added followed by addition of methyl 2-hydroxyacetate (8.0 ml, 0.103 mmoles) at 25° C. under nitrogen atmosphere and the reaction mixture was stirred at 80-90° C. for 18 h. The reaction mixture was poured into ice cold water and extracted with ethyl acetate. The combined ethyl acetate extract was washed with water & brine, dried over sodium sulphate and evapourated under reduced pressure. The crude product was purified by column chromatography (Eluent: 16% ethyl acetate in hexane) to yield 1.25 gm (23%) of product as off white solid.

$^1$H NMR: DMSO-$d_6$, δ 2.55 (s, 3H), 3.67 (s, 3H), 5.02 (s, 2H), 7.04 (dd, J=8.8 & 0.4 Hz, 1H), 8.20 (dd, J=8.8 & 2.4 Hz, 1H), 8.78 (d, J=2.0 Hz, 1H).

Step 2: Methyl 2-((5-(1-(hydroxyimino)ethyl)pyridin-2-yl)oxy)acetate

To a solution of methyl 2-((5-acetylpyridin-2-yl)oxy)acetate (1.23 gm, 0.059 mole) in ethanol (10 mL), a solution of sodium acetate (0.942 gm, 0.0117 mole) and hydroxylammonium chloride (1.2 gm, 0.0117 mole) in water (5 ml) was added and the reaction mixture was refluxed for 1 h. The reaction mixture was coiled to room temperature and solvent was evapourated in vacuum. The residue was diluted with ice cold water and solid seperated was filtered, washed with water and dried over $P_2O_5$ under vacuum to yield 1.15 gm (88%) of title product as off white solid.

$^1$H NMR: DMSO-$d_6$, δ 2.12 (s, 3H), 3.66 (s, 3H), 4.94 (s, 2H), 6.95 (d, J=8.8 Hz, 1H), 8.02 (dd, J=8.4 & 2.4 Hz, 1H), 8.34 (d, J=2.0 Hz, 1H).

Step 3: Methyl 2-((5-(1-(((4-(trifluoromethyl)benzyl)oxy)imino)ethyl)pyridin-2-yl)oxy)acetate To a solution of 1-(bromomethyl)-4-(trifluoromethyl)benzene (0.87 ml, 5.6 mmoles) in DMF (10 mL), cesium carbonate (3.35 gm, 10.2 mmoles) was added followed by addition of methyl 2-((5-(1-(hydroxyimino)ethyl)pyridin-2-yl)oxy)acetate (1.15 gm, 5.1 mmoles) at 25° C. under nitrogen atmosphere and the reaction mixture was stirred at the same temperature for 12 h. The reaction mixture was poured into ice cold water and extracted with ethyl acetate. The combined ethyl acetate extract was washed with water & brine, dried over sodium sulphate and evapourated under reduced pressure to yield 2.0 gm (94%) of product as thick liquid.

$^1$H NMR: DMSO-$d_6$, δ 2.24 (s, 3H), 3.65 (s, 3H), 4.94 (s, 2H), 5.29 (s, 2H), 6.94 (d, J=8.8 Hz, 1H), 7.60 (d, J=8.0 Hz, 2H), 7.73 (d, J=8.0 Hz, 2H), 8.00 (dd, J=8.8 & 2.4 Hz, 1H), 8.36 (d, J=2.4 Hz, 1H).

Step 4: 2-((5-(1-(((4-(trifluoromethyl)benzyl)oxy)imino)ethyl)pyridin-2-yl)oxy)acetic acid To a solution of the product of step 3 (2.0 gm, 5.2 mmoles) in a mixture of THF (12 mL), methanol (4 mL) and water (4 mL), lithium hydroxide (440 mg, 10.5 mmoles) was added and the reaction mixture was stirred at ambient temperature for 4 hours. The solvents were evaporated under reduced pressure. The residue was dissolved in water, acidified with 1N HCl and extracted with ethyl acetate. The combined ethyl acetate extract was washed with water & brine, dried over sodium sulphate and evapourated under reduced pressure to yield 1.7 gm (88%) of title product as white solid.

$^1$H NMR: DMSO-$d_6$, δ 2.24 (s, 3H), 4.84 (s, 2H), 5.29 (s, 2H), 6.93 (d, J=8.8 Hz, 1H), 7.60 (d, J=8.0 Hz, 2H), 7.73 (d, J=8.0 Hz, 2H), 7.98 (dd, J=8.8 & 2.8 Hz, 1H), 8.36 (d, J=2.4 Hz, 1H).

Example 3

N-((tetrahydro-2H-pyran-4-yl)methyl)-2-((5-(1-(((4-(trifluoromethyl) benzyl)oxy)imino)ethyl)pyridin-2-yl)oxy)acetamide To a solution of compound prepared in example 3 (2.0 gm, 5.43 mmoles) in DMF (10 mL), (tetrahydro-2H-pyran-4-yl)methanamine (625 mg, 5.43 mmoles), HOBT (1.09 gm, 8.14 mmoles), EDC.HCl (1.25 gm, 6.52 mmoles) and N-ethyl morpholine (2.05 mL, 16.29 mmoles) were added and reaction mixture was srirred at 25° C. for 5 hours under nitrogen atmosphere. The reaction mixture was poured into ice cold water and extracted with ethyl acetate. The combined ethyl acetate extract was washed with water & brine, dried over sodium sulphate and evaporated under reduced pressure. The crude product was triturated with hexane to yield 2.8 gm (72%) of product as white solid.

$^1$H NMR: DMSO-$d_6$ δ 1.07-1.11 (m, 2H), 1.45-1.49 (m, 2H), 1.58-1.64 (m, 1H), 2.24 (s, 3H), 2.96 (t, J=6.8 Hz, 2H), 3.17-3.23 (m, 2H), 3.22 (dd, J=11.4 & 2.6 Hz, 2H), 4.72 (s, 2H), 5.29 (s, 2H), 6.91 (d, J=8.8 Hz, 1H), 7.60 (d, J=8.0 Hz, 2H) 7.72 (d, J=8.0 Hz, 2H), 7.98-7.99 (m, 1H), 8.33 (d, J=2.0 Hz, 1H).

Example 4

N-((tetrahydro-2H-pyran-4-yl)methyl)-2-((5-(1-(((4-(trifluoromethyl) benzyl)oxy)imino)ethyl)pyridin-2-yl)amino)acetamide

Step 1: ethyl 2-((5-acetylpyridin-2-yl)amino)acetate

To a mixture of 1-(6-aminopyridin-3-yl)ethanone (700 mg, 5.15 mmoles) and perchloric acid (1.4 ml), a solution of glyoxal (0.24 ml, 5.15 mmoles) in methanol (14 ml) was added and reaction mixture was refluxed for 48 hrs. The reaction mixture was poured into ice cold water and extracted with ethyl acetate. The combined ethyl acetate extract was washed with water & brine, dried over sodium sulphate and evapourated under reduced pressure. The crude product was purified by column chromatography (Eluent: 1.5% methanol in chloroform) to yield 350 mg (33%) of product as off white solid.

$^1$H NMR: DMSO-$d_6$ δ 2.43 (s, 3H), 3.63 (s, 3H), 4.12 (d, J=6.0 Hz, 2H), 6.62 (dd, J=8.8 Hz, 1H), 7.86 (dd, J=8.8 & 2.4 Hz, 1H), 8.34 (d, J=2.0 Hz, 1H).

Step 2: 2-((5-acetylpyridin-2-yl)amino)acetic acid

To a solution of the product of step 1 (1.1 gm, 5.3 mmoles) in a mixture of THF (12 ml), methanol (4 ml) and water (4 ml), lithium hydroxide (444 mg, 10.6 mmoles) was added and the reaction mixture was stirred at ambient temperature for 4 hours. The solvents were evaporated under reduced pressure. The residue was dissolved in water, acidified with 1N HCl and evaporated in vacuum. The residue was diluted with ethyl acetate, stirred for 30 min and filtered. The filtrate was concentrated in vacuum to yield 1.0 gm (98%) of title product as off white solid.

$^1$H NMR: CD$_3$OD: δ2.48 (s, 3H), 4.08 (s, 2H), 6.59 (dd, J=8.8 Hz, 1H), 7.86 (dd, J=8.8 & 2.0 Hz, 1H), 8.65 (d, J=2.4 Hz, 1H).

Step 3: N-((tetrahydro-2H-pyran-4-yl)methyl)-2-((5-(1-(((4-(trifluoromethyl) benzyl)oxy)imino)ethyl) pyridin-2-yl)amino)acetamide To a solution of the product of step 2 (1.4 gm, 7.2 mmoles) in DMF (10 mL), (tetrahydro-2H-pyran-4-yl)methanamine (1.2 gm, 7.94 mmoles), HOBT (1.48 gm, 10.8 mmoles), EDC.HCl (1.16 gm, 8.66 mmoles) and N-ethyl morpholine (2.75 mL, 21.6 mmoles) were added and reaction mixture was srirred at 25° C. for 2 hours under nitrogen atmosphere.

The reaction mixture was poured into ice cold water and extracted with ethyl acetate. The combined ethyl acetate extract was washed with water & brine, dried over sodium sulphate and evaporated under reduced pressure to yield 1.0 gm of crude product as an oil.

The crude product was dissolved in ethanol (10 ml) and a solution of sodium acetate (0.564 gm, 6.8 mmoles) and hydroxylammonium chloride (0.615 gm, 6.8 mmoles) in water (5 ml) was added and the reaction mixture was refluxed for 1 h. The reaction mixture was cooled to room temperature and solvent was evapourated in vacuum. The residue was diluted with ice cold water and extarcted with ethyl acetate. The ethyl acetate extract was washed with water & brine, dried over sodium sulphate and evaporated in vacuum to yield 420 mg of product as an oil.

To a solution of product obtained above (450 mg, 1.47 mmoles) in DMF (5 mL), cesium carbonate (959 mg, 2.94 mmoles) was added followed by addition of 1-(bromomethyl)-4-(trifluoromethyl)benzene (350 mg, 1.47 mmoles) at 25° C. under nitrogen atmosphere and the reaction mixture was stirred at the same temperature for 12 h. The reaction mixture was poured into ice cold water and extracted with ethyl acetate. The combined ethyl acetate extract was washed with water and brine, dried over sodium sulphate and evapourated under reduced pressure to yield 135 mg (58%) product as off white solid.

$^1$H NMR: DMSO-d$_6$, δ 1.22-1.25 (m, 2H), 1.47-1.50 (m, 2H), 1.57-1.62 (m, 1H), 2.17 (s, 3H), 2.95 (t, J=6.4 Hz, 2H), 3.16-3.22 (m, 2H), 3.78-3.81 (dd, J=2.8 & 11.2 Hz, 2H), 3.85 (d, J=6.0 Hz, 2H), 5.23 (s, 2H), 6.55 (d, J=9.2 Hz, 1H), 7.11 (t, J=5.8 Hz, 1H), 7.59 (d, J=8.0 Hz, 2H), 7.65-7.68 (dd, J=2.4 & 8.8 Hz, 1H), 7.73 (d, J=8.4 Hz, 2H), 7.83 (t, J=6.0 Hz, —NH), 8.19 (s, 1H).

Example 5

N-((tetrahydro-2H-pyran-4-yl)methyl)-2-((4-(1-(((4-(trifluoromethyl)benzyl)oxy)imino)propyl)phenyl) amino)acetamide

Step 1: N-(4-(1-(((4-(Trifluoromethyl)benzyl)oxy) imino)propyl)phenyl)acetamide To a solution of N-(4-(1-(hydroxyimino)propyl)phenyl) acetamide (6 gm, 0.0291 moles) in DMF (60 mL), cesium carbonate (18.9 gm, 0.0582 moles) and 4-(trifluoromethyl) benzyl bromide (6.96 gm, 0.0291 moles) were added and the reaction mixture was srirred at 25° C. for 3 hours. The reaction mixture was poured into ice cold water and extracted with ethyl acetate. The combined ethyl acetate extract was washed with water & brine, dried over sodium sulphate and evaporated under reduced pressure to yield 10 gm (94%) of product as solid.

$^1$H NMR: DMSO-d$_6$ δ 1.06 (t, J=7.4 Hz, 3H), 2.04 (s, 3H), 2.75 (q, J=7.6 Hz, 2H), 5.27 (s, 2H), 7.55-7.61 (m, 6H), 7.73 (d, J=8 Hz, 2H), 10.07 (s, 1H).

Step 2: 1-(4-Aminophenyl)propan-1-one O-(4-(trifluoromethyl)benzyl)oxime

To a solution of the product of step 1 (10 g, 0.0275 moles) in ethanol (70 ml), a solution of potassium hydroxide (6.15 g, 0.1098 moles) in water (30 ml) was added and the reaction mixture was stirred at 80-90° C. for 36 hours. The reaction mixture was poured into ice cold water and extracted by dichloromethane. The combined dichloromethane extract was washed with water and brine, dried over sodium sulphate and evapourated under reduced pressure to yield 7.5 gm (84%) of product as liquid.

$^1$H NMR: DMSO-d$_6$ δ 1.03 (t, J=3.8 Hz, 3H), 2.66 (q, J=7.6 Hz, 2H), 5.21 (s, 2H), 5.42 (s, 2H), 6.51-6.56 (m, 2H), 7.30-7.35 (m, 2H), 7.57 (d, J=8 Hz, 2H), 7.72 (d, J=8.4 Hz, 2H).

Step 3: Ethyl 2-((4-(1-(((4-(trifluoromethyl)benzyl) oxy)imino)propyl)phenyl)amino)acetate To a solution of the product of step 2 (3.5 g, 0.0097 moles) in DMF (35 mL), potassium carbonate (4 gm, 0.0291 moles) and Ethyl bromo acetate (1.8 gm, 0.0107 moles) were added and reaction mixture was srirred at 100° C. for over night. The reaction mixture was poured into ice cold water and extracted by ethyl acetate. The combined ethyl acetate extract was washed with water and brine, dried over sodium sulphate and evapourated under reduced pressure to yield 2.2 gm (55%) of product as solid.

$^1$H NMR: DMSO-d$_6$ δ 1.04 (t, J=7.6 Hz, 3H), 1.19 (t, J=7.2 Hz, 3H), 2.67 (q, J=7.6 Hz, 2H), 3.90 (d, J=6.4 Hz, 2H), 4.10 (q, J=7.2 Hz, 2H), 5.22 (s, 2H), 6.37 (t, J=6.4 Hz, 1H), 6.52 (d, J=8.8 Hz, 2H), 7.37 (d, J=8.8 Hz, 2H), 7.58 (d, J=8.4 Hz, 2H), 7.72 (d, J=8.4 Hz, 2H).

Step 4: 2-((4-(1-(((4-(Trifluoromethyl)benzyl)oxy) imino)propyl)phenyl)amino)acetic acid To a solution of the product of step 3 (2.2 g, 5.39 mmoles) in THF (10 ml), a solution of lithium hydroxide (0.45 g, 10.77 mmoles) in water (10 mL) was added and the reaction mixture was stirred at 25° C. for 3 hours. The solvents were evaporated under reduced pressure. The residue was dissolved in water and neutralized to pH 6 with 1N HCl. Solid seperated was filtered, washed with water and dried over CaCl$_2$ under vacuum to give 1.64 g (82%) of title product.

$^1$H NMR: DMSO-d$_6$, δ 1.04 (t, J=7.6 Hz, 3H), 2.66-2.71 (m, 2H), 3.80 (s, 2H), 5.21 (s, 2H), 6.52 (d, J=8.8 Hz, 2H), 7.37 (d, J=8.8 Hz, 2H), 7.58 (d, J=8 Hz, 2H), 7.72 (d, J=8.4 Hz, 2H).

Step 5: N-((Tetrahydro-2H-pyran-4-yl)methyl)-2-((4-(1-(((4-(trifluoromethyl)benzyl)oxy)imino)propyl)phenyl)amino)acetamide To a solution of the product of step 4 (6.5 g, 0.0171 moles) in DMF (40 mL), (tetrahydro-2H-pyran-4-yl)methanamine hydrochloride (2.6 gm, 0.0171 moles), HOBT (2.31 gm, 0.0171 moles), EDC.HCl (4.24 gm, 0.0222 moles) and N-ethyl morpholine (5.9 gm, 0.0513 moles) were added and reaction mixture was srirred at 25° C. for 5 hours under nitrogen atmosphere. The reaction mixture was poured into ice cold water and extracted with ethyl acetate. The combined ethyl acetate extract was washed with water & brine, dried over sodium sulphate and evapourated under reduced pressure. The crude product was purified by coloumn chromatography using 1% MeOH in chloroform as eluent to yield 1.22 g (15%) of product as white solid.

$^1$H NMR: DMSO-d$_6$, δ 1.03 (t, J=7.6 Hz, 3H), 1.06-1.10 (m, 2H), 1.44 (d, J=12.8 Hz, 2H), 1.58-1.61 (m, 1H), 2.69 (q, J=7.6 Hz, 2H), 2.96 (t, J=6.4 Hz, 2H), 3.15-3.22 (m, 2H), 3.64 (d, J=6 Hz, 2H), 3.77 (dd, J=11.6 & 2.8 Hz, 2H), 5.21 (s, 2H), 6.25 (t, J=6 Hz, 1H), 6.51 (d, J=8.8 Hz, 2H), 7.37 (d, J=8.8 Hz, 2H), 7.57 (d, J=8.0 Hz, 2H), 7.72 (d, J=8.0 Hz, 2H), 7.89 (t, J=6.0 Hz, 1H).

Example 6

2,2'-((5-(1-(((4-(trifluoromethyl)benzyl)oxy)imino) ethyl)oxazol-2-yl)azanediyl)diacetic acid Step 1: Diethyl 2,2'-((5-acetyloxazol-2-yl)azanediyl) diacetate To a solution of 1-(2-aminooxazol-5-yl)ethanone (300 mg, 2.38 mmoles) in DMF (2 mL), cesium carbonate (1.16 gm, 3.57 mmoles) was added followed by addition of ethyl bromoacetate (794 mg, 4.76 mmoles) at 25° C. under nitrogen atmosphere and the reaction mixture was stirred at the same temperature for 18 h. The reaction mixture was poured into ice cold water and extracted with ethyl acetate. The combined ethyl acetate extract was washed with water & brine, dried over sodium sulphate and evaporated under reduced pressure to yield 310 mg (44%) of product as thick liquid.

$^1$H NMR: δ 1.27 (t, J=7.0 Hz, 6H), 2.33 (s, 3H), 4.20-4.27 (m, 4H), 4.37 (s, 4H), 7.57 (s, 1H).

Step 2: Diethyl 2,2'-((5-(1-(hydroxyimino)ethyl) oxazol-2-yl)azanediyl)diacetate To a solution of diethyl 2,2'-((5-acetyloxazol-2-yl) azanediyl)diacetate (300 mg, 1.01 mmoles) in ethanol (6 mL), a solution of sodium acetate (165 mg, 2.01 mmoles) and hydroxylammonium chloride (139 mg gm, 2.01 mmoles) in water (2 ml) was added and the reaction mixture was refluxed for 1 h. The reaction mixture was cooled to room temperature and solvent was evapourated in vacuum. The residue was diluted with ice cold water and extracted with ethyl acetate. The combined ethyl acetate extract was washed with water & brine, dried over sodium sulphate and evaporated under reduced pressure to yield 252 mg (80%) of title product as thick liquid.

$^1$H NMR: δ 1.25-1.37 (m, 6H), 2.45 (s, 3H), 4.18-4.29 (m, 4H), 4.37 (s, 4H), 7.57 (s, 1H).

Step 3: Diethyl 2,2'-((5-(1-(((4-(trifluoromethyl)benzyl)oxy)imino)ethyl)oxazol-2-yl)azanediyl)diacetate To a solution of 1-(bromomethyl)-4-(trifluoromethyl)benzene (200 mg, 0.84 mmoles) in DMF (2 mL), cesium carbonate (408 mg, 1.26 mmoles) was added followed by addition of diethyl 2,2'-((5-(1-(hydroxyimino)ethyl)oxazol-2-yl) azanediyl)diacetate (262 mg, 0.84 mmoles) at 25° C. under nitrogen atmosphere and the reaction mixture was stirred at the same temperature for 18 h. The reaction mixture was poured into ice cold water and extracted with ethyl acetate. The combined ethyl acetate extract was washed with water & brine, dried over sodium sulphate and evapourated under reduced pressure. The crude product was purified by column chromatography (Eluent: 15% ethyl acetate in hexane) to yield 295 mg (75%) product as thick liquid.

$^1$H NMR: δ 1.25-1.36 (m, 6H), 2.04 (s, 3H), 4.19 (q, J=7.2 Hz, 4H), 4.32 (s, 4H), 5.22 (s, 2H), 6.99 (s, 1H), 7.47 (d, J=8.0 Hz, 2H), 7.60 (d, J=8.4 Hz, 2H).

Step 4: 2,2'-((5-(1-(((4-(trifluoromethyl)benzyl)oxy) imino)ethyl)oxazol-2-yl)azanediyl)diacetic acid To a solution of the product of step 3 (295 mg, 0.62 mmoles) in a mixture of THF (6 ml), methanol (2 ml) and water (2 ml), lithium hydroxide (105 mg, 1.25 mmoles) was added and the reaction mixture was stirred at ambient temperature for 4 hours. The solvents were evaporated under reduced pressure. The residue was dissolved in water and acidified with 1N HCl. White solid seperated was filtered and washed with water & dried over P$_2$O$_5$ under vacuum to give 250 mg (82%) of title product as off white solid.

$^1$H NMR: DMSO-d$_6$ δ 2.06 (s, 3H), 4.16 (s, 4H), 5.23 (s, 2H), 7.31 (s, 1H), 7.58 (d, J=8.0 Hz, 2H), 7.72 (d, J=8.4 Hz, 2H).

Example 7

2,2'-((5-(1-(((4-(trifluoromethyl)benzyl)oxy)imino) ethyl)oxazol-2-yl)azanediyl)bis(N-((tetrahydro-2H-pyran-4-yl)methyl)acetamide)

To a solution of compound prepared in example 6 (250 mg, 0.60 mmoles) in DMF (2 mL), (tetrahydro-2H-pyran-4-yl) methanamine (138 mg, 1.20 mmoles), HOBT (121 mg, 0.90 mmoles), EDC.HCl (138 mg, 0.72 mmoles) and N-ethyl morpholine (227 μL, 1.80 mmoles) were added and reaction mixture was srirred at 25° C. for 2-5 hours under nitrogen atmosphere. The reaction mixture was poured into ice cold water and extracted with ethyl acetate. The combined ethyl acetate extract was washed with water & brine, dried over sodium sulphate and evaporated under reduced pressure. The crude product was triturated with hexane to yield 180 mg (49%) of product as white solid.

$^1$H NMR: DMSO-d$_6$, δ 1.04-1.14 (m, 4H), 1.47-1.50 (m, 4H), 1.58-1.62 (m, 2H), 2.04 (s, 3H), 2.96 (t, J=6.2 Hz, 4H), 3.18 (t, J=10.8 Hz, 4H), 3.76 (dd, J=11.0 Hz & 3.0 Hz, 4H), 4.08 (s, 4H), 5.20 (s, 2H), 7.28 (s, 1H), 7.58 (d, J=8.0 Hz, 2H), 7.72 (d, J=8.4 Hz, 2H).

Example 8

2-((1-(4-(trifluoromethyl)benzyl)-3-((((4-(trifluoromethyl)benzyl)oxy)imino)methyl)-1H-indol-5-yl) oxy)acetic acid Step 1: ethyl 2-((1H-indol-5-yl)oxy)acetate To a solution of 5-hydroxy indole (4.56 gm, 0.034 moles) in DMF (20 ml), potassium carbonate (9.43 gm, 0.068 moles), ethyl bromoacetate (6.29 gm, 0.0377 moles) were added and the reaction mixture was stirred at ambient temperature for 12 hours. The reaction mixture was poured into ice cold water and extracted with ethyl acetate. The combined ethyl acetate extract was washed with water & brine, dried over sodium sulphate and evapourated under reduced pressure to yield 6.2 gm (82%) of product as solid.

$^1$H NMR: DMSO-d$_6$, δ 1.20 (t, J=3.6 Hz, 3H), 4.13 (q, J=8.6 Hz, 2H), 4.70 (s, 2H), 6.31 (d, J=2.0 Hz, 1H), 6.74 (dd,

J=8.8 & 2.4 Hz, 1H), 6.99 (d, J=2.4 Hz, 1H), 7.27 (dd, J=5.6 & 2.8 Hz, 2H), 10.95 (bs, 1H).

Step 2: ethyl 2-((3-((hydroxyimino)methyl)-1H-indol-5-yl)oxy)acetate

To DMF (1.74 gm, 0.023 moles) cooled to 0° C. under nitrogen atmosphere, Phosphorous oxy chloride (3.5 gm, 0.022 moles) was added in portions and stireed for 15 mins. To this was added a solution of the product of step 1 (2.5 gm, 0.011 mole) in dichloro ethane (18 ml) at 0° C. and heated to 80° C. for 2 hrs. The solvents were evaporated under reduced pressure. The residue was dissolved in water, basified with NaOH and extracted with ethyl acetate. The ethyl acetate extract was washed with water & brine, dried over sodium sulphate and evaporated under reduced pressure. The crude product was purified by column chromatography (eluent: 40% EtOAC in hexane) to yield 900 mg (31%) of product as solid.
$^1$H NMR: DMSO-$d_6$ δ 1.22 (t, J=1.82 Hz, 3H), 4.15 (q, J=7.2 Hz, 2H), 4.77 (s, 2H), 6.91 (dd, J=8.8 & 2.8 Hz, 1H), 7.41 (d, J=8.8 Hz, 1H), 7.52 (d, J=2.4 Hz, 1H), 8.23 (d, J=2.8 Hz, 1H), 9.88 (d, J=4.4 Hz, 1H), 12.06 (bs, 1H).

Step 3: ethyl 2-((3-((hydroxyimino)methyl)-1H-indol-5-yl)oxy)acetate

To a solution of the product of step 2 (880 mg, 3.56 mmoles) in methanol (6 mL) and water (3 mL), hydroxylamine hydrochloride (491 mg, 7.12 mmoles), sodium acetate (584 mg, 7.12 moles were added and the reaction mixture was heated at 70° C. for 2 hours. The reaction mixture was poured into ice cold water and extracted with ethyl acetate. The combined ethyl acetate extract was washed with water & brine, dried over sodium sulphate and evaporated under reduced pressure, The crude product was purified by column chromatography using 40% EtOAC in hexane as eluent to yield 280 mg (27%) of product as solid.
$^1$H NMR: δ 1.21 (t, J=4.0 Hz, 3H), 4.14 (q, J=7.0 Hz, 2H), 4.70 (s, 2H), 6.83 (dd, J=8.8 & 2.4 Hz, 1H), 7.31 (d, J=8.8 Hz, 1H), 7.43 (d, J=2.4 Hz, 1H), 7.58 (d, J=2.8 Hz, 1H), 8.22 (s, 1H), 10.46 (s, 1H), 11.30 (bs, 1H).

Step 4: ethyl 2-((1-(4-(trifluoromethyl)benzyl)-3-((((4-(trifluoromethyl)benzyl)oxy)imino)methyl)-1H-indol-5-yl)oxy)acetate To a solution of the product of step 3 (280 mg, 1.068 mmoles) in DMF (2 ml), cesium carbonate (1.0 gm, 3.2 mmoles), 4-trifluoromethyl benzylbromide (510 mg, 2.13 mmoles were added and the reaction mixture was stirred at 25° C. for 2 hours. The reaction mixture was poured into ice cold water and extracted with ethyl acetate. The combined ethyl acetate extract was washed with water & brine, dried over sodium sulphate and evaporated under reduced pressure, The crude product was purified by column chromatography using 15% EtOAC in hexane as eluent to yield 350 mg (56%) of product as solid.
$^1$H NMR: δ 1.16 (t, J=7.0 Hz, 3H), 4.11 (q, J=6.9 Hz, 2H), 4.69 (s, 2H), 5.23 (s, 2H), 5.54 (s, 2H), 6.85 (dd, J=8.8 & 2.4 Hz, 1H), 7.35-7.40 (m, 4H), 7.68 (d, J=2.4 Hz, 4H), 7.74 (d, J=8.0 Hz, 2H), 7.85 (s, 1H), 8.44 (s, 1H).

Step 5: 2-((1-(4-(trifluoromethyl)benzyl)-3-((((4-(trifluoromethyl)benzyl)oxy)imino)methyl)-1H-indol-5-yl)oxy)acetic acid To a solution of the product of step 4 (350 mg, 0.605 mmoles) in THF (2 mL) Water: (2 ml), lithum hydroxide monohydrate (38 mg, 0.908 mmoles), was added and the reaction mixture was stirred at 25° C. for 3 hours. The reaction mixture was poured into ice cold water, acidified by dil.HCl and extracted with ethyl acetate. The combined ethyl acetate extract was washed with water & brine, dried over sodium sulphate and evaporated under reduced pressure to yield 250 mg (77%) of product as solid.
$^1$H NMR: δ 4.61 (s, 2H), 5.21 (s, 2H), 5.53 (s, 2H), 6.84 (dd, J=9.2 & 2.8 Hz, 1H), 7.36 (t, 3H), 7.42 (d, J=2.4 Hz, 1H), 7.67 (d, J=8.4 Hz, 4H), 7.74 (d, J=8.4 Hz, 2H), 7.84 (s, 1H), 8.42 (s, 1H), 12.98 (d, J=4.4 Hz, 1H)

Example 9

N-((tetrahydro-2H-pyran-4-yl)methyl)-2-((1-(4-(trifluoromethyl)benzyl)-3-((((4-(trifluoromethyl)benzyl)oxy)imino)methyl)-1H-indol-5-yl)oxy)acetamide To a solution of compound prepared in example 8 (250 mg, 0.454 mmoles) in DMF (2 mL), (tetrahydro-2H-pyran-4-yl) methanamine hydrochloride (83 mg, 0.545 mmoles), HOBT (Catalyst), EDC.HCl (130 mg, 0.681 mmoles) and N-ethyl morpholine (0.173 ml, 1.362 mmoles) were added and the reaction mixture was srirred at 25° C. for 5 hours under nitrogen atmosphere. The reaction mixture was poured into ice cold water and extracted with ethyl acetate. The combined ethyl acetate extract was washed with water & brine, dried over sodium sulphate and evaporated under reduced pressure. The crude product was purified by column chromatography to yield 200 mg (68%) of product as white solid.
$^1$H NMR: δ 1.01-1.11 (m, 2H), 1.42 (d, J=12.8 Hz, 2H), 1.61-1.67 (m, 1H), 2.67 (t, J=1.8 Hz, 2H), 2.98-3.15 (m, 2H), 3.71 (dd, J=14.0 & 2.8 Hz, 2H), 4.45 (s, 2H), 5.23 (s, 2H), 5.53 (s, 2H), 6.89 (dd, J=8.8 & 2.4 Hz, 1H), 7.34 (d, J=8.0 Hz, 2H), 7.38 (d, J=9.2 Hz, 1H), 7.46 (d, J=2.4 Hz, 1H), 7.68 (t, J=8.2 Hz, 4H), 7.75 (d, J=8.0 Hz, 2H), 7.84 (s, 1H), 8.08 (t, J=6.0 Hz, 1H), 8.42 (s, 1H).

Example 10

2-(2-methyl-4-(2-phenyl-1-(((4-(trifluoromethyl)benzyl)oxy)imino)ethyl)phenoxy)-N-((tetrahydro-2H-pyran-4-yl)methyl)acetamide $^1$H NMR: δ 1.2 (m, 2H), 1.5 (m, 2H), 1.7 (m, 1H), 2.2 (s, 3H), 3.2 (t, J=6.4 Hz, 2H), 3.3 (t, J=11.4 Hz, 2H), 3.9 (dd, J=11.6 & 3.6 Hz, 2H), 4.1 (s, 2H), 4.6 (s, 2H), 5.2 (s, 2H), 6.6 (t, NH), 6.7 (d, J=8.4 Hz, 1H), 7.1-7.2 (m, 5H), 7.3 (m, 3H), 7.5 (s, 1H), 7.6 (d, J=8.0 Hz, 2H).

Example 11

2-(4-(2-phenyl-1-(((4-(trifluoromethyl)benzyl)oxy)imino)ethyl)phenoxy)-N-((tetrahydro-2H-pyran-4-yl)methyl)acetamide $^1$H NMR: DMSO-$d_6$, δ 1.02-1.13 (m, 2H), 1.43-1.46 (m, 2H), 1.58-1.65 (m, 1H), 2.97 (t, J=6.4 Hz, 2H), 3.15-3.20 (m, 2H), 3.75 (dd, J=11.4 & 2.6 Hz, 2H), 4.17 (s, 2H), 4.47 (s, 2H), 5.31 (s, 2H), 6.89 (d, J=9.2 Hz, 2H), 7.12-7.16 (m, 3H), 7.20-7.24 (m, 2H), 7.55-7.61 (m, 4H), 7.71 (d, J=8.0 Hz, 2H), 8.80 (t, NH).

Example 12

2-(4-(2-phenyl-1-(((3-(trifluoromethyl)benzyl)oxy)imino)ethyl)phenoxy)-N-((tetrahydro-2H-pyran-4-yl)methyl)acetamide $^1$H NMR: DMSO-$d_6$, δ, 1.11-1.06 (m, 2H) 1.46-1.43 (m, 2H), 1.64-1.59 (m, 1H), 2.99 (t, J=12.8 Hz, 2H), 3.19 (t, J=21.6 Hz, 2H), 3.78 (d, 2H), 4.16 (s, 2H), 4.47 (s, 2H), 5.31 (s, 2H), 6.91 (d, J=8.8 Hz, 2H), 7.15 (t, J=3.8 Hz, 3H), 7.22 (d, J=6 Hz, 2H), 7.60 (t, J=8.8 Hz, 3H), 7.67 (s, 1H), 7.70 (s, 2H), 8.10 (t, J=11.6 Hz, 1H).

Example 13

2-(4-(2-(pyridin-4-yl)-1-(((4-(trifluoromethyl)benzyl)oxy)imino)ethyl)phenoxy)-N-((tetrahydro-2H-pyran-4-yl)methyl)acetamide $^1$H NMR: DMSO-d$_6$, δ 1.05-1.10 (m, 2H), 1.45 (d, J=12.8 Hz, 2H), 1.65-1.71 (m, 1H), 2.98 (t, J=6.4 Hz, 2H), 3.14-3.20 (m, 2H), 3.75-3.78 (m, 2H), 4.20 (s, 2H), 4.47 (s, 2H), 5.30 (s, 2H), 6.92 (d, J=8.8 Hz, 2H), 7.14 (d, J=6.0 Hz, 2H), 7.55 (d, J=8.0 Hz, 2H), 7.61 (d, J=8.8 Hz, 2H), 7.71 (d, J=8.0 Hz, 2H), 8.07 (s, —NH), 8.40 (d, J=4.4 Hz, 2H).

Example 14

2-(4-(2-morpholino-1-(((4-(trifluoromethyl)benzyl)oxy)imino)ethyl)phenoxy)-N-((tetrahydro-2H-pyran-4-yl)methyl)acetamide $^1$H NMR: DMSO-d$_6$, δ 1.05-1.16 (m, 2H), 1.48 (d, J=13.2 Hz, 2H), 1.62-1.68 (m, 1H), 2.36 (br s, 4H), 3.01 (t, J=6.4 Hz, 2H), 3.20 (t, J=11.0 Hz, 2H), 3.46 (m, 4H), 3.64 (s, 2H), 3.78-3.81 (dd, J=11.6 & 2.4 Hz, 2H), 4.51 (s, 2H), 5.27 (s, 2H), 6.93 (d, J=8.8 Hz, 2H), 7.61 (d, J=8.0 Hz, 2H), 7.67 (d, J=8.8 Hz, 2H), 7.74 (d, J=8.4 Hz, 2H), 8.11 (t, NH).

Example 15

N-((tetrahydro-2H-pyran-4-yl)methyl)-2-(4-(2-thiomorpholino-1-(((4-(trifluoromethyl) benzyl)oxy)imino)ethyl)phenoxy)acetamide $^1$H NMR: DMSO-d$_6$, δ 1.09-1.18 (m, 2H), 1.46-1.49 (m, 2H), 1.60-1.65 (m, 1H), 2.47-2.49 (m, 4H), 2.61-2.63 (m, 4H), 2.99 (t, J=6.6 Hz, 2H), 3.17-3.23 (m, 2H), 3.67 (s, 2H), 3.78-3.81 (m, 2H), 4.50 (s, 2H), 5.26 (s, 2H), 6.92 (dd, J=7.0 & 1.8 Hz, 2H), 7.59-7.65 (m, 4H), 7.73 (d, J=8.0 Hz, 2H), 8.09 (t, NH).

Example 16

2-(2-methyl-4-(2-(thiophen-3-yl)-1-(((4-(trifluoromethyl)benzyl)oxy)imino)ethyl)phenoxy)-N-((tetrahydro-2H-pyran-4-yl)methyl)acetamide $^1$H NMR: DMSO-d$_6$, δ 1.04-1.14 (m, 2H), 1.44 (d, J=12.8 Hz, 2H), 1.58-1.67 (m, 1H), 2.19 (s, 3H), 2.98 (t, J=6.4 Hz, 2H), 3.15-3.21 (m, 2H), 3.76-3.79 (m, 2H), 4.11 (s, 2H), 4.50 (s, 2H), 5.31 (s, 2H), 6.77 (d, J=8.8 Hz, 1H), 6.89 (m, 1H), 7.11 (s, 1H), 7.38-7.40 (m, 1H), 7.43 (dd, J=8.6 & 1.8 Hz, 1H), 7.51 (s, 1H), 7.55 (d, J=8.0 Hz, 2H), 7.70 (d, J=8.4 Hz, 2H), 7.90 (t, NH).

Example 17

N-((tetrahydro-2H-pyran-4-yl)methyl)-2-(4-((((4-(trifluoromethyl) benzyl)oxy)imino)methyl)phenoxy)acetamide $^1$H NMR: DMSO-d$_6$, δ 1.05-1.16 (m, 2H), 1.46-1.49 (m, 2H), 1.62-1.98 (m, 1H), 2.99 (t, J=6.4 Hz, 2H), 3.17-3.24 (m, 2H), 3.78-3.81 (m, 2H), 4.51 (s, 2H), 5.23 (s, 2H), 6.97-6.99 (dd. J=2.0 & 8.8 Hz, 2H), 7.54 (dd, J=2.0 & 8.8 Hz, 2H), 7.60 (d, J=8.0 Hz, 2H), 7.73 (d, J=8.0 Hz, 2H), 8.12 (t, NH), 8.29 (s, 1H).

Example 18

N-((tetrahydro-2H-pyran-4-yl)methyl)-2-(4-(1-(((4-(trifluoromethyl)benzyl)oxy)imino)ethyl)phenoxy)acetamide $^1$H NMR: DMSO-d$_6$, δ 1.12-1.07 (m, 2H), 1.45-1.44 (m, 2H), 1.48 (m, 1H), 2.21 (s, 3H), 2.99 (t, J=6.4 Hz, 2H), 3.22-3.16 (m, 2H), 3.80-3.77 (m, 2H), 4.49 (s, 2H), 5.26 (s, 2H), 6.96-6.93 (dd, J=2.0 & 6.8 Hz, 2H), 7.60-7.56 (m, 4H), 7.71 (d, J=8.0 Hz, 2H), 8.10 (t, J=5.6 Hz, 1H).

Example 19

N-((tetrahydro-2H-pyran-4-yl)methyl)-2-((5-((((4-(trifluoromethyl) benzyl)oxy)imino)methyl)pyridin-2-yl)oxy)acetamide $^1$H NMR: δ 1.24-1.35 (m, 2H), 1.54-1.58 (m, 2H), 1.73-1.81 (m, 1H), 3.21 (t, J=6.6 Hz, 2H), 3.31-3.37 (m, 2H), 3.93-3.97 (m, 2H), 4.85 (s, 2H), 5.23 (s, 2H), 6.42 (bs, NH), 6.83 (d, J=8.4 Hz, 1H), 7.49 (d, J=8.0 Hz, 2H), 7.61 (d, J=8.0 Hz, 2H), 7.95 (dd, J=8.4 & 2.4 Hz, 1H), 8.12 (s, 1H), 8.20 (d, J=2.4 Hz, 1H).

Example 20

N-((tetrahydro-2H-pyran-4-yl)methyl)-2-((4-(1-(((4-(trifluoromethyl) benzyl)oxy)imino)ethyl)phenyl)amino)acetamide $^1$H NMR: DMSO-d$_6$, δ 1.06-1.15 (m, 2H), 1.44 (d, J=12.8 Hz, 2H), 1.60 (m, 1H), 2.16 (s, 3H), 2.94 (t, J=6.4 Hz, 2H), 3.16-3.22 (m, 2H), 3.64 (d, J=6.0 Hz, 2H), 3.77-3.80 (m, 2H), 5.22 (s, 2H), 6.23 (t, J=6.0 Hz, 1H), 6.51 (d, J=8.4 Hz, 2H), 7.38 (d, J=8.4 Hz, 2H), 7.58 (d, J=8 Hz, 2H), 7.71 (d, J=8.0 Hz, 2H), 7.88 (t, J=5.8 Hz, 1H).

Example 21

2-((5-(1-(((4-cyanobenzyl)oxy)imino)ethyl)pyridin-2-yl)oxy)-N-((tetrahydro-2H-pyran-4-yl)methyl)acetamide $^1$H NMR: DMSO-d$_6$, δ 1.06-1.10 (m, 2H), 1.44-1.47 (m, 2H), 1.62-1.68 (m, 1H), 2.24 (s, 3H), 2.95 (t, J=6.4 Hz, 2H), 3.15-3.22 (m, 2H), 3.76-3.80 (dd, J=2.8 & 11.6 Hz, 2H), 4.71 (s, 2H), 5.27 (s, 2H), 6.91 (d, J=8.8 Hz, 1H), 7.57 (d, J=8.0 Hz, 2H), 7.83 (d, J=6.4 Hz, 2H), 7.95-8.01 (m. 2H), 8.32 (s, 1H).

Example 22

N-((tetrahydro-2H-pyran-4-yl)methyl)-2-((5-(1-(((4-(trifluoromethyl)benzyl)oxy)imino)propyl)pyridin-2-yl)oxy)acetamide $^1$H NMR: δ 1.14 (t, J=7.6 Hz, 3H), 1.24-1.34 (m, 2H), 1.55-1.58 (m, 2H), 1.72-1.82 (m, 1H), 2.76 (q, J=7.6 Hz, 2H), 3.23 (t, J=6.4 Hz, 2H), 3.30-3.37 (m, 2H), 3.93-3.97 (m, 2H), 4.85 (s, 2H), 5.25 (s, 2H), 6.44 (bs, NH), 6.81 (d, J=8.8 Hz, 1H), 7.48 (d, J=8.0 Hz, 2H), 7.61 (d, J=8.0 Hz, 2H), 7.94 (dd, J=8.6 & 2.2 Hz, 1H), 8.35 (d, J=2.4 Hz, 1H).

Example 23

N-((tetrahydro-2H-pyran-4-yl)methyl)-2-((5-(1-(((4-(trifluoromethyl)benzyl)oxy)imino)propyl)pyridin-2-yl)amino)acetamide $^1$H NMR: δ 1.03 (t, J=7.6 Hz, 3H), 1.07-1.11 (m, 2H), 1.47-1.51 (m, 2H), 1.57-1.63 (m, 1H), 2.68 (q, J=7.6 Hz, 2H), 2.94 (t, J=6.4 Hz, 2H), 3.16-3.23 (m, 2H), 3.78 (dd, J=11.2 & 2.4 Hz, 2H), 3.86 (d, J=6.0 Hz, 2H), 5.23 (s, 2H), 6.55 (d, J=8.8 Hz, 1H), 7.12 (t, J=6.0 Hz, NH), 7.58 (d, J=8.0 Hz, 2H) 7.64 (dd, J=9.0 & 2.6 Hz, 1H), 7.72 (d, J=8.0 Hz, 2H), 7.83 (t, J=6.0 Hz, NH), 8.18 (d, J=2.0 Hz, 1H).

Example 24

2-((5-(1-((benzyloxy)imino)propyl)pyridin-2-yl)oxy)-N-((tetrahydro-2H-pyran-4-yl)methyl)acetamide $^1$H NMR: δ 1.11 (t, J=7.6 Hz, 3H), 1.24-1.35 (m, 2H), 1.54-1.58 (m, 2H), 1.72-1.82 (m, 1H), 2.72 (q, J=7.6 Hz, 2H), 3.21 (t, J=6.6 Hz, 2H), 3.31-3.37 (m, 2H), 3.93-3.96 (m, 2H), 4.84 (s, 2H), 5.21 (s, 2H), 6.45 (bs, NH), 6.80 (dd, J=8.8 & 0.4 Hz, 1H), 7.29-7.41 (m, 5H), 7.96 (dd, J=8.8 & 2.4 Hz, 1H), 8.35 (d, J=2.0 Hz, 1I4).

Example 25

2-((5-(1-(((4-methylbenzyl)oxy)imino)propyl)pyridin-2-yl)oxy)-N-((tetrahydro-2H-pyran-4-yl)methyl)acetamide $^1$H NMR: δ 1.10 (t, J=7.2 Hz, 3H), 1.25-1.36 (m, 2H), 1.56-1.59 (m, 2H), 1.73-1.84 (m, 1H), 2.36 (s, 3H), 2.72 (q, J=7.2 Hz, 2H), 3.22 (t, J=6.6 Hz, 2H), 3.32-3.38 (m, 2H), 3.94-3.98 (m, 2H), 4.85 (s, 2H), 5.27 (s, 2H), 6.47 (bs, NH), 6.82 (d, J=8.4 Hz, 1H), 7.17 (d, J=7.6 Hz, 2H), 7.29 (d, J=8.0 Hz, 2H), 7.98-8.00 (m, 1H), 8.35 (d, J=2.0 Hz, 1H).

Example 26

2-((5-(1-(((4-methoxybenzyl)oxy)imino)propyl)pyridin-2-yl)oxy)-N-((tetrahydro-2H-pyran-4-yl)methyl)acetamide $^1$H NMR: δ 1.10 (t, J=7.6 Hz, 3H), 1.24-1.35 (m, 2H), 1.54-1.56 (m, 2H), 1.73-1.80 (m, 1H), 2.69 (q, J=7.6 Hz, 2H), 3.21 (t, J=6.6 Hz, 2H), 3.31-3.37 (m, 2H), 3.81 (s, 3H), 3.93-3.96 (m, 2H), 4.84 (s, 2H), 5.13 (s, 2H), 6.45 (bs, NH), 6.81 (d, J=8.8 Hz, 1H), 6.88-6.91 (m, 2H), 7.31-7.35 (m, 2H), 7.96 (dd, J=8.8 & 2.4 Hz, 1H), 8.34 (d, J=2.0 Hz, 1H).

Example 27

2-((5-(1-(((4-fluorobenzyl)oxy)imino)propyl)pyridin-2-yl)oxy)-N-((tetrahydro-2H-pyran-4-yl)methyl)acetamide $^1$H NMR: δ 1.11 (t, J=7.6 Hz, 3H), 1.24-1.35 (m, 2H), 1.54-1.58 (m, 2H), 1.73-1.81 (m, 1H), 2.71 (q, J=7.6 Hz, 2H), 3.21 (t, J=6.6 Hz, 2H), 3.31-3.37 (m, 2H), 3.93-3.96 (m, 2H), 4.84 (s, 2H), 5.16 (s, 2H), 6.45 (bs, NH), 6.81 (dd, J=8.8 & 0.4 Hz, 1H), 7.01-7.07 (m, 2H), 7.34-7.39 (m, 2H), 7.95 (dd, J=8.8 & 2.4 Hz, 1H), 8.34 (d, J=2.0 Hz, 1H).

Example 28

2-((5-(1-(((4-cyanobenzyl)oxy)imino)propyl)pyridin-2-yl)oxy)-N-((tetrahydro-2H-pyran-4-yl)methyl)acetamide $^1$H NMR: δ 1.16 (t, J=7.6 Hz, 3H), 1.25-1.35 (m, 2H), 1.55-1.59 (m, 2H), 1.72-1.81 (m, 1H), 2.75 (q, J=7.6 Hz, 2H), 3.21 (t, J=6.6 Hz, 2H), 3.31-3.38 (m, 2H), 3.93-3.97 (m, 2H), 4.85 (s, 2H), 5.26 (s, 2H), 6.44 (bs, NH), 6.82 (dd, J=8.8 Hz, 1H), 7.47 (d, J=8.0 Hz, 2H), 7.65 (d, J=8.4 Hz, 2H), 7.93 (dd, J=8.4 & 2.4 Hz, 1H), 8.35 (d, J=2.0 Hz, 1H).

Example 29

2-(2-methyl-4-(1-(((4-(trifluoromethyl)benzyl)oxy)imino)butyl)phenoxy)-N-((tetrahydro-2H-pyran-4-yl)methyl)acetamide $^1$H NMR: DMSO-d$_6$, δ 0.87 (t, J=7.4 Hz, 3H), 1.07-1.15 (m, 2H), 1.41-1.48 (m, 4H), 1.60-1.67 (m, 1H), 2.21 (s, 3H), 2.72 (t, J=7.6 Hz, 2H), 3.00 (t, J=6.4 Hz, 2H), 3.16-3.22 (t, J=12.0 Hz, 2H), 3.77-3.80 (dd, J=11.2 & 11.2 Hz, 2H), 4.51 (s, 2H), 5.24 (s, 2H), 6.80 (d, J=8.4 Hz, 1H), 7.36-7.38 (dd, J=8.8 & 8.4 Hz, 1H), 7.43 (d, J=1.6 Hz, 1H), 7.58 (d, J=8.0 Hz, 2H), 7.72 (d, J=8.0 Hz, 2H), 7.93 (t, J=5.8 Hz, 1H).

Example 30

2-(4-(2-methoxy-1-(((4-(trifluoromethyl)benzyl)oxy)imino)ethyl)phenoxy)-N-((tetrahydro-2H-pyran-4-yl)methyl)acetamide $^1$H NMR: DMSO-d$_6$, δ 1.07-1.04 (m, 2H), 1.15-1.13 (m, 2H), 1.66-1.62 (m, 1H), 3.00 (t, 2H), 3.16-3.17 (m, 2H), 3.19 (s, 3H), 3.80-3.77 (m, 2H), 4.49 (s, 2H), 4.58 (s, 2H), 5.27 (s, 2H), 6.95-6.93 (dd, J=2 & 7.2 Hz, 2H), 7.55-7.52 (m, 2H), 7.59 (d, J=8 Hz, 2H), 7.72 (d, J=8.0 Hz, 2H), 8.09 (t, J=5.9 Hz, 1H).

Example 31

2-(4-(2-hydroxy-1-(((4-(trifluoromethyl)benzyl)oxy)imino)ethyl)phenoxy)-N-((tetrahydro-2H-pyran-4-yl)methyl)acetamide $^1$H NMR: DMSO-d$_6$, δ 1.05-1.15 (m, 2H), 1.46 (d, J=12.8 Hz, 2H), 1.62-1.68 (m, 1H), 2.99 (t, J=6.4 Hz, 2H), 3.17 (t, J=10.8 Hz, 2H), 3.77-3.81 (m, 2H), 4.49 (s, 2H), 4.60 (d, J=5.6 Hz, 2H), 5.15 (t, J=5.6 Hz, 1H), 5.25 (s, 2H), 6.93 (d, J=8.8 Hz, 2H), 7.55 (d, J=8.8 Hz, 2H), 7.59 (d, J=8 Hz, 2H), 7.71 (d, J=8 Hz, 2H), 8.09 (t, J=5.6 Hz, 1H).

Example 32

2-(2-methyl-4-(1-(((4-methylbenzyl)oxy)imino)-2-phenylethyl)phenoxy)-N-((tetrahydro-2H-pyran-4-yl)methyl)acetamide $^1$H NMR: DMSO-d$_6$, δ 1.03-1.16 (m, 2H), 1.43 (m, 2H), 1.58-1.66 (m, 1H), 2.18 (s, 3H), 2.28 (s, 3H), 2.97 (t, J=6.6 Hz, 2H), 3.1-3.20 (m, 2H), 3.75-3.79 (m, 2H), 4.10 (s, 2H), 4.48 (s, 2H), 5.15 (s, 2H), 6.74 (d, J=8.8 Hz, 1H), 7.10-7.16

(m, 5H), 7.18-7.21 (m, 2H), 7.24 (d, J=8.0 Hz, 2H), 7.40 (dd, J=8.6 & 2.2 Hz, 1H), 7.50 (d, J=1.6 Hz, 1H), 7.91 (t, J=6.0 Hz, NH)

Example 33

2-(4-(1-(((4-methylbenzyl)oxy)imino)-2-phenyl-ethyl)phenoxy)-N-((tetrahydro-2H-pyran-4-yl)methyl)acetamide $^1$H NMR: DMSO-d$_6$, δ 1.06-1.16 (m, 2H), 1.43 (d, J=12.8 Hz, 2H), 1.59-1.66 (m, 1H), 2.28 (s, 3H), 2.96 (t, J=6.4 Hz, 2H), 3.14 (m, 2H), 3.75-3.78 (m, 2H), 4.11 (s, 2H), 4.46 (s, 2H), 5.16 (s, 2H), 6.89 (d, J=8.8 Hz, 2H), 7.11-7.16 (m, 5H), 7.18-7.22 (m, 2H), 7.24 (d, J=8.0 Hz, 2H), 7.59 (d, J=8.8 Hz, 2H), 8.07 (t, J=5.8 Hz, NH).

Example 34

2-(4-(1-(((4-fluorobenzyl)oxy)imino)-2-phenyl-ethyl)-2-methylphenoxy)-N-((tetrahydro-2H-pyran-4-yl)methyl)acetamide $^1$H NMR: DMSO-d$_6$, 1.21-1.36 (m, 2H), 1.54-1.57 (m, 2H), 1.72-1.79 (m, 1H), 2.25 (s, 3H), 3.23 (t, J=6.4 Hz, 2H), 3.31-3.37 (m, 2H), 3.93 (dd, J=11.2 & 3.6 Hz, 2H), 4.11 (s, 2H), 4.48 (s, 2H), 5.20 (s, 2H), 6.68 (d, J=8.8 Hz, 2H), 6.98 (t, J=8.8 Hz, 2H), 7.13-7.32 (m, 7H), 7.39 (dd, J=8.8 & 2.0 Hz, 1H), 7.52 (s, 1H).

Example 35

2-(4-(1-(((4-fluorobenzyl)oxy)imino)-2-phenylethyl)phenoxy)-N-((tetrahydro-2H-pyran-4-yl)methyl)acetamide $^1$H NMR: δ 1.24-1.35 (m, 2H), 1.54-1.57 (m, 2H), 1.71-1.80 (m, 1H), 3.23 (t, J=6.2 Hz, 2H), 3.29-3.36 (m, 2H), 3.92-3.96 (m, 2H), 4.12 (s, 2H), 4.47 (s, 2H), 5.20 (s, 2H), 6.58 (s, 1H), 6.85 (d, J=12 Hz, 2H), 6.98-7.03 (m, 2H), 7.13-7.24 (m, 5H), 7.29-7.32 (m, 2H), 7.58-7.61 (m, 2H).

Example 36

2-(4-(14((4-chlorobenzyl)oxy)imino)-2-phenyl-ethyl)-2-methylphenoxy)-N-((tetrahydro-2H-pyran-4-yl)methyl)acetamide $^1$H NMR: DMSO-d$_6$, δ 1.03-1.14 (m, 2H), 1.43 (d, J=12.8 Hz, 2H), 1.59-1.65 (m, 1H), 2.18 (s, 3H), 2.97 (t, J=6.4 Hz, 2H), 3.15-3.20 (m, 2H), 3.75-3.79 (m, 2H), 4.12 (s, 2H), 4.49 (s, 2H), 5.19 (s, 2H), 6.75 (d, J=8.8 Hz, 1H), 7.12-7.15 (m, 3H), 7.19-7.22 (m, 2H), 7.35-7.43 (m, 5H), 7.58 (d, J=1.2 Hz, 1H), 7.90 (t, J=5.8 Hz, NH).

Example 37

2-(4-(1-(((4-chlorobenzyl)oxy)imino)-2-phenylethyl)phenoxy)-N-((tetrahydro-2H-pyran-4-yl)methyl)acetamide $^1$H NMR: DMSO-d$_6$, δ 1.05-1.13 (m, 2H), 1.43 (d, J=11.6 Hz, 2H), 1.61-1.63 (m, 1H), 2.96 (t, J=6.4 Hz, 2H), 3.14 (t, J=10.8 Hz, 2H), 3.75-3.78 (m, 2H), 4.13 (s, 2H), 4.46 (s, 2H), 5.20 (s, 2H), 6.89 (d, J=8.8 Hz, 2H), 7.12-7.15 (m, 3H), 7.19-7.23 (m, 2H), 7.36-7.42 (m, 4H), 7.58 (d, J=8.8 Hz, 2H), 8.06 (t, J=5.8 Hz, NH).

Example 38

2-(2-methyl-4-(2-phenyl-1-(((4-(trifluoromethoxy)benzyl)oxy)imino)ethyl)phenoxy)-N-((tetrahydro-2H-pyran-4-yl)methyl)acetamide $^1$H NMR: δ 1.25-1.37 (m, 2H), 1.57 (m, 2H), 1.71-1.80 (m, 1H), 2.25 (s, 3H), 3.25 (t, J=6.6 Hz, 2H), 3.31-3.37 (m, 2H), 3.93-3.97 (m, 2H), 4.13 (s, 2H), 4.48 (s, 2H), 5.23 (s, 2H), 6.58 (s, 1H), 6.70 (d, J=8.8 Hz, 1H), 7.14-7.24 (m, 7H), 7.33 (d, J=8.8 Hz, 2H), 7.39-7.42 (m, 1H), 7.51 (d, J=7.6 Hz, 1H).

Example 39

2-(4-(2-phenyl-1-(((4-(trifluoromethoxy)benzyl)oxy)imino)ethyl)phenoxy)-N-((tetrahydro-2H-pyran-4-yl)methyl)acetamide $^1$H NMR: DMSO-d$_6$, δ 1.02-1.13 (m, 2H), 1.43 (d, J=12.8 Hz, 2H), 1.58-1.65 (m, 1H), 2.96 (t, J=6.4 Hz, 2H), 3.14-3.20 (m, 2H), 3.75-3.78 (m, 2H), 4.14 (s, 2H), 4.47 (s, 2H), 5.24 (s, 2H), 6.89 (d, J=8.8 Hz, 2H), 7.13-7.14 (m, 3H), 7.18-7.22 (m, 2H), 7.33 (d, J=8.4 Hz, 2H), 7.47 (d, J=8.8 Hz, 2H), 7.59 (d, J=8.8 Hz, 2H), 8.06 (t, J=5.8 Hz, NH).

Example 40

2-(4-(1-(((4-methoxybenzyl)oxy)imino)-2-phenyl-ethyl)-2-methylphenoxy)-N-((tetrahydro-2H-pyran-4-yl)methyl)acetamide $^1$H NMR: DMSO-d$_6$, δ 1.03-1.14 (m, 2H), 1.43-1.47 (m, 2H), 1.59-1.64 (m, 1H), 2.18 (s, 3H), 2.97 (t, J=6.4 Hz, 2H), 3.14-3.20 (m, 2H), 3.73 (s, 3H), 3.75-3.79 (m, 2H), 4.08 (s, 2H), 4.48 (s, 2H), 5.12 (s, 2H), 6.74 (d, J=8.8 Hz, 1H), 6.88-6.92 (m, 2H), 7.10-7.13 (m, 3H), 7.17-7.21 (m, 2H), 7.29-7.32 (m, 2H), 7.40 (dd, J=8.6 & 2.2 Hz, 1H), 7.50 (d, J=1.6 Hz, 1H), 7.91 (t, J=6.0 Hz, NH)

Example 41

2-(4-(1-(((4-methoxybenzyl)oxy)imino)-2-phenyl-ethyl)phenoxy)-N-((tetrahydro-2H-pyran-4-yl)methyl)acetamide $^1$H NMR: DMSO-d$_6$, δ 1.03-1.13 (m, 2H), 1.43-1.46 (m, 2H), 1.59-1.65 (m, 1H), 2.96 (t, J=6.4 Hz, 2H), 3.14-3.20 (m, 2H), 3.73 (s, 3H), 3.75-3.78 (m, 2H), 4.10 (s, 2H), 4.46 (s, 2H), 5.13 (s, 2H), 6.89 (dd, J=8.8 & 2.0 Hz, 4H), 7.10-7.13 (m, 3H), 7.18-7.21 (m, 2H), 7.29 (dd, J=11.2 & 2.8 Hz, 2H), 7.58 (d, J=10.0 Hz, 2H), 8.06 (t, J=6.0 Hz, NH).

Example 42

2-(4-(1-(((4-(methylsulfonyl)benzyl)oxy)imino)propyl)phenoxy)-N-((tetrahydro-2H-pyran-4-yl)methyl)acetamide $^1$H NMR: δ 1.04-1.16 (m, 5H), 1.45-1.49 (m, 2H), 1.61-1.70 (m, 1H), 2.72 (q, J=7.6 Hz, 2H), 2.99 (t, J=6.4 Hz, 2H), 3.17-3.23 (m, 5H), 3.77-3.81 (dd, J=11.4 & 2.6 Hz, 2H), 4.51 (s, 2H), 5.28 (s, 2H), 6.95-6.98 (m, 2H), 7.55-7.59 (m, 2H), 7.62 (d, J=8.0 Hz, 2H), 7.91 (dd, J=6.8 & 1.6 Hz, 2H), 8.08 (t, J=5.8 Hz, NH).

Example 43

2-(4-(2-phenyl-1-((pyridin-2-ylmethoxy)imino)ethyl)phenoxy)-N-((tetrahydro-2H-pyran-4-yl)methyl)acetamide $^1$H NMR: δ 1.27-1.35 (m, 2H), 1.53-1.57 (m, 2H), 1.72-1.79 (m, 1H), 3.21 (t, J=6.6 Hz, 2H), 3.29-3.36 (m, 2H), 3.92 (dd, J=11.0 & 3.4 Hz, 2H), 4.21 (s, 2H), 4.47 (s, 2H), 5.39 (s, 2H), 6.58 (bs, NH), 6.82-6.86 (m, 2H), 7.16-7.28 (m, 7H), 7.60-7.64 (m, 3H), 8.56-8.58 (m, 1H).

Example 44

2-(4-(1-((2-(1H-indol-1-yl)ethoxy)imino)propyl)phenoxy)-N-((tetrahydro-2H-pyran-4-yl)methyl)acetamide $^1$H NMR: DMSO-d$_6$, δ 0.83 (t, J=7.4 Hz, 3H), 1.08-1.12 (m, 2H), 1.45-1.49 (m, 2H), 1.60-1.68 (m, 1H), 2.49-2.53 (m, 2H), 3.00 (t, J=6.4 Hz, 2H), 3.20 (t, J=11.6 Hz, 2H), 3.78-3.81 (dd, J=11.4 & 2.6 Hz, 2H), 4.36-4.38 (t, J=5.0 Hz, 2H), 4.48-4.51 (m, 4H), 6.41 (d, J=3.2 Hz, 1H), 6.94 (d, J=8.8 Hz, 2H), 6.97-7.01 (m, 1H), 7.08 (t, J=7.0 Hz, 1H), 7.30 (d, J=2.8 Hz, 1H), 7.44 (d, J=8.0 Hz, 1H), 7.51-7.56 (m, 3H), 8.10 (t, NH).

Example 45

2-(4-(1-(((5-ethylpyrimidin-2-yl)oxy)imino)propyl)phenoxy)-N-((tetrahydro-2H-pyran-4-yl)methyl)acetamide $^1$H NMR: DMSO-d$_6$, δ 1.07-1.20 (m, 8H), 1.47-1.50 (dd, J=12.8 & 12.8 Hz, 2H), 1.65-1.66 (m, 1H), 2.56-2.61 (q, 2H), 2.86-2.92 (q, 2H), 3.02 (t, J=6.4 Hz, 2H), 3.18-3.28 (m, 2H), 3.78-3.81 (dd, J=11.2 & 11.2 Hz, 2H), 4.55 (s, 2H), 7.03-7.06 (m, 2H), 7.73-7.76 (m, 2H), 8.13 (t, J=5.8 Hz, 1H), 8.54 (s, 2H).

Example 46

2-(4-(1-(((5-methyl-2-phenyloxazol-4-yl)methoxy)imino)propyl)phenoxy)-N-((tetrahydro-2H-pyran-4-yl)methyl)acetamide $^1$H NMR: δ 1.07 (t, J=7.6 Hz, 3H), 1.25-1.37 (m, 2H), 1.56-1.64 (m, 2H), 1.75-1.81 (m, 1H), 2.47 (s, 3H), 2.71 (q, J=7.6 Hz, 2H), 3.23 (t, J=6.6 Hz, 2H), 3.32 (t, J=11.8 Hz, 2H), 3.94 (dd, J=11.0 & 3.8 Hz, 2H), 4.51 (s, 2H), 5.12 (s, 2H), 6.62 (bs, NH), 6.88-6.92 (m, 2H), 7.40-7.45 (m, 3H), 7.59-7.63 (m, 2H), 7.99-8.02 (m, 2H).

Example 47

2-(4-(1-(((3-(tert-butyl)-1-(p-tolyl)-1H-pyrazol-5-yl)methoxy)imino)propyl)phenoxy)-N-((tetrahydro-2H-pyran-4-yl)methyl)acetamide $^1$H NMR: δ 1.06 (t, J=7.6 Hz, 3H), 1.27-1.34 (m, 2H), 1.36 (s, 9H), 1.58-1.60 (m, 2H), 1.78-1.80 (m, 1H), 2.37 (s, 3H), 2.69 (q, J=7.4 Hz, 2H), 3.24 (t, J=6.6 Hz, 2H), 3.32 (t, J=11.6 Hz, 2H), 3.94 (dd, J=11.0 & 3.4 Hz, 2H), 4.52 (s, 2H), 5.11 (s, 2H), 6.37 (s, 1H), 6.62 (s, NH), 6.90 (d, J=8.8 Hz, 2H), 7.21 (d, J=8.0 Hz, 2H), 7.44 (d, J=8.0 Hz, 2H), 7.58 (d, J=8.8 Hz, 2H).

Example 48

N-((tetrahydro-2H-pyran-4-yl)methyl)-2-((5-(((4-(trifluoromethyl)benzyl)oxy)imino)-5,6,7,8-tetrahydronaphthalen-2-yl)oxy)acetamide $^1$H NMR: DMSO-d$_6$, δ 1.08 (t, J=6.6 Hz, 2H), 1.44 (d, J=12.8 Hz, 2H), 1.48 (m, 1H), 1.75 (t, J=5.8 Hz, 2H), 2.66 (t, J=5.6 Hz, 2H), 2.98 (t, J=6.6 Hz, 2H), 3.01 (t, J=6.4 Hz, 2H), 3.16-3.21 (m, 2H), 3.80 (d, J=2.4 Hz, 2H), 4.47 (s, 2H), 5.24 (s, 2H), 6.74 (d, J=2.4 Hz, 1H), 6.77-6.80 (dd, J=2.8 & 8.8 Hz, 1H), 7.58 (d, J=8 Hz, 2H), 7.69-7.73 (dd, J=4 & 8 Hz, 3H), 8.09 (t, J=5.6 Hz, 1H).

Example 49

2-((5-(((4-chlorobenzyl)oxy)imino)-5,6,7,8-tetrahydronaphthalen-2-yl)oxy)-N-((tetrahydro-2H-pyran-4-yl)methyl)acetamide $^1$H NMR: DMSO-d$_6$, δ 1.09-1.15 (m, 2H), 1.45 (d, J=12.8 Hz, 2H), 1.61-1.69 (m, 1H), 1.69-7.75 (m, 2H), 2.63-2.68 (m, 4H), 2.99 (t, J=6.4 Hz, 2H), 3.15-3.22 (m, 2H), 4.47 (s, 2H), 5.12 (s, 2H), 6.73 (d, J=2.4 Hz, 1H), 6.78-6.81 (dd, J=2.8 & 8.8 Hz, 1H), 7.38 (d, J=8 Hz, 4H), 7.71 (d, J=8.8 Hz, 1H), 8.08 (t, J=6.0 Hz, 1H).

Example 50

2-((5-(((4-cyanobenzyl)oxy)imino)-5,6,7,8-tetrahydronaphthalen-2-yl)oxy)-N-((tetrahydro-2H-pyran-4-yl)methyl)acetamide $^1$H NMR: DMSO-d$_6$, δ 1.07-1.30 (m, 2H), 1.44-1.48 (m, 2H), 1.64 (m, 1H), 1.72-1.75 (m, 2H), 2.66 (t, J=6.0 Hz, 2H), 2.69-2.72 (m, 2H), 2.99 (t, J=6.4 Hz, 2H), 3.16-3.22 (m, 2H), 3.76-3.80 (q, J=2.6 Hz, 2H), 4.47 (s, 2H), 5.23 (s, 2H), 6.74 (d, J=2.8 Hz, 1H), 6.77-6.8 (dd, J=2.4 & 8.4 Hz, 1H), 7.54 (d, J=8.4 Hz, 2H), 7.68 (d, J=8.8 Hz, 1H), 7.81 (d, J=1.6 Hz, 2H), 8.08 (t, J=6.0 Hz, 1H).

Example 51

2-((5-(((4-methoxybenzyl)oxy)imino)-5,6,7,8-tetrahydronaphthalen-2-yl)oxy)-N-((tetrahydro-2H-pyran-4-yl)methyl)acetamide $^1$H NMR: DMSO-d$_6$, δ 1.09-1.16 (m, 2H), 1.46-1.49 (dd, J=1.6 & 12.8 Hz, 2H), 1.64-1.74 (m, 3H), 2.61-2.66 (m, 4H), 2.99 (t, J=6.4 Hz, 2H), 3.18-3.24 (m, 2H), 3.74 (s, 3H), 3.78-3.82 (dd, J=2.4 & 11.2 Hz, 2H), 4.48 (s, 2H), 5.06 (s, 2H), 6.75 (d, J=2.4 Hz, 1H), 6.80-6.83 (dd, J=2.8 & 8.8 Hz, 1H), 6.92 (d, J=8.4 Hz, 2H), 7.34 (d, J=8.4 Hz, 2H), 7.77 (d, J=8.8 Hz, 1H), 8.08 (t, J=6.0 Hz, 1H)

Example 52

Methyl 3-(((((6-(2-oxo-2-(((tetrahydro-2H-pyran-4-yl)methyl)amino)ethoxy)-3,4-dihydronaphthalen-1(2H)-ylidene)amino)oxy)methyl)benzoate $^1$H NMR: DMSO-d$_6$, δ 1.08-1.15 (m, 2H), 1.45-1.49 (dd, J=1.6 & 12.8 Hz, 2H), 1.64-1.66 (m, 1H), 1.72 (t, J=6.0 Hz, 2H), 2.65-2.71 (m, 4H), 2.99 (t, J=6.4 Hz, 2H), 3.17-3.20 (m, 2H), 3.78-3.81 (dd, J=2.4 & 11.2 Hz, 2H), 3.85 (s, 3H), 4.48 (s, 2H), 5.22 (s, 2H), 6.75 (d, J=2.8 Hz, 1H), 6.79-6.82 (dd, J=2.8 & 8.8 Hz, 1H), 7.50 (t, J=7.6 Hz, 1H), 7.68 (d, J=7.6 Hz, 1H), 7.74 (d, J=8.8 Hz, 1H), 7.88-7.91 (m, 1H), 7.98 (s, 1H), 8.06 (t, J=6.0 Hz, 1H).

Example 53

2-((5-(1-(((4-(trifluoromethyl)benzyl)oxy)imino) ethyl)quinolin-8-yl)oxy)acetic acid $^1$H NMR: DMSO-$d_6$, δ 2.36 (s, 3H), 4.78 (s, 2H), 5.32 (s, 2H), 7.23 (d, J=7.6 Hz, 1H), 7.41-7.44 (m, 1H), 7.55-7.58 (m, 1H), 7.64-7.66 (m, 2H), 7.77 (d, J=8.4 Hz, 2H), 8.40 (d, J=8.8 Hz, 1H), 8.86 (d, J=2.8 Hz, 1H).

Example 54

N-((tetrahydro-2H-pyran-4-yl)methyl)-245-(1-(((4-(trifluoromethyl)benzyl)oxy)imino)ethyl)quinolin-8-yl)oxy)acetamide $^1$H NMR: DMSO-$d_6$, δ 1.09-1.16 (m, 2H), 1.44 (d, J=12.8 Hz, 2H), 1.61-1.64 (m, 1H), 2.36 (s, 3H), 3.04 (t, J=6.4 Hz, 2H), 3.16-3.23 (m, 2H), 3.77 (dd, J=2.8 & 11.6 Hz, 2H), 4.77 (s, 2H), 5.33 (s, 2H), 7.24 (d, J=8.4 Hz, 1H), 7.43 (dd, J=4.4 & 8.8 Hz, 1H), 7.58 (d, J=8.4 Hz, 1H), 7.64 (d, J=8 Hz, 2H), 7.77 (d, J=8 Hz, 2H), 8.34 (t, J=5.8 Hz, 1H), 8.39 (dd, J=1.6 & 8.8 Hz, 1H), 8.89 (dd, J=1.6 & 4.0 Hz, 1H).

Example 55

2-methyl-N-((tetrahydro-2H-pyran-4-yl)methyl)-2-(4-(1-(((4-(trifluoromethyl)benzyl)oxy)imino)propyl)phenoxy)propanamide $^1$H NMR: δ 1.14 (t, J=7.6 Hz, 3H), 1.23-1.34 (m, 2H), 1.50-1.51 (m, 2H), 1.57 (s, 6H), 1.72-1.77 (m, 1H), 2.74 (q, J=7.6 Hz, 2H), 3.17 (t, J=6.6 Hz, 2H), 3.29-3.36 (m, 2H), 3.91-3.95 (m, 2H), 5.25 (s, 2H), 6.68 (t, J=5.8 Hz, NH), 6.86-6.90 (m, 2H), 7.49-7.55 (m, 4H), 7.60 (d, J=8.4 Hz, 2H).

Example 56

2-methyl-N-((tetrahydro-2H-pyran-4-yl)methyl)-2-(4-(1-(((4-(trifluoromethyl)benzyl)oxy)imino)ethyl)phenoxy)propanamide $^1$H NMR: δ 1.23-1.34 (m, 2H), 1.51-1.56 (comp, 8H), 1.71-1.77 (m, 1H), 2.26 (s, 3H), 3.17 (t, J=6.6 Hz, 2H), 3.29-3.36 (m, 2H), 3.92-3.95 (m, 2H), 5.26 (s, 2H), 6.71 (t, J=5.6 Hz, NH), 6.86-6.90 (m, 2H), 7.49-7.55 (m, 4H), 7.60 (d, J=8.0 Hz, 2H).

Example 57

2-(4-(1-(((tetrahydro-2H-pyran-4-yl)methoxy)imino) ethyl)phenoxy)-N-((tetrahydro-2H-pyran-4-yl)methyl)acetamide $^1$H NMR: DMSO, δ 1.09-1.16 (m, 2H), 1.23-1.31 (m, 2H), 1.50 (dd, J=12.8 & 1.6 Hz, 2H), 1.61 (dd, J=12.8 & 2 Hz, 2H), 1.62-1.66 (m, 1H), 1.67-1.96 (m, 1H), 2.15 (s, 3H), 3.01 (t, J=6.4 Hz, 2H), 3.18-3.24 (m, 2H), 3.26-3.29 (m, 2H), 3.78-3.86 (m, 4H), 3.97 (d, J=6.4 Hz, 2H), 4.51 (s, 2H), 6.97 (dd, J=7.2 & 2.4 Hz, 2H), 7.60 (dd, J=6.8 & 2.0 Hz, 2H), 8.12 (t, J=5.8 Hz, 1H)

Example 58

2-(4-(1-((cyclohexylmethoxy)imino)ethyl)phenoxy)-N-((tetrahydro-2H-pyran-4-yl)methyl)acetamide $^1$H NMR: DMSO-$d_6$, δ 0.95-0.98 (m, 2H), 1.09-1.21 (m, 5H), 1.48 (dd, J=12.8 & 1.6 Hz, 2H), 1.64-1.74 (m, 7H), 2.14 (s, 3H), 3.01 (t, J=6.6 Hz, 2H), 3.18-3.24 (m, 2H), 3.82 (dd, J=11.2 & 2.4 Hz, 2H), 3.92 (d, J=6.4 Hz, 2H), 4.51 (s, 2H), 6.94-6.98 (m, 2H), 7.57-7.60 (m, 2H), 8.12 (t, J=6 Hz, 1H).

Example 59

2-(4-(1-((naphthalen-2-ylmethoxy)imino)ethyl)phenoxy)-N-((tetrahydro-2H-pyran-4-yl)methyl)acetamide $^1$H NMR: DMSO-$d_6$, δ 1.05-1.16 (m, 2H), 1.46 (d, J=13.2 Hz, 2H), 1.63-1.68 (m, 1H), 2.22 (s, 3H), 3.01 (t, J=6.4 Hz, 2H), 3.16-3.23 (m, 2H), 3.78-3.82 (dd, J=11.2 & 2.4 Hz, 2H), 4.50 (s, 2H), 5.33 (s, 2H), 6.97 (d, J=7.2 Hz, 2H), 7.49-7.52 (m, 2H), 7.54-7.56 (dd, J=8.8 & 1.6 Hz, 1H), 7.59-7.61 (dd, J=6.8 & 1.6 Hz, 2H), 7.89-7.93 (m, 4H), 8.11 (t, J=5.8 Hz, 1H).

The following compounds can be prepared by procedure similar to those described above with appropriate variations of reactions, reaction conditions and quantities of reagents which are within the scope of persons skilled in the art.

Example 60

2-((5-(1-(((4-(trifluoromethyl)benzyl)oxy)imino) ethyl)pyridin-2-yl)amino)acetic acid

Example 61

2-((5-((((4-(trifluoromethyl)benzyl)oxy)imino)methyl)pyridin-2-yl)oxy)acetic acid

Example 62

2-((5-(1-(((4-cyanobenzyl)oxy)imino)ethyl)pyridin-2-yl)oxy)acetic acid

Example 63

2-((5-(1-(((4-(trifluoromethyl)benzyl)oxy)imino) propyl)pyridin-2-yl)oxy)acetic acid

Example 64

2-((5-(1-(((4-(trifluoromethyl)benzyl)oxy)imino) propyl)pyridin-2-yl)amino)acetic acid

Example 65

2-((5-(1-((benzyloxy)imino)propyl)pyridin-2-yl)oxy)acetic acid

Example 66

2-((5-(1-(((4-methylbenzyl)oxy)imino)propyl)pyridin-2-yl)oxy)acetic acid

Example 67

2-((5-(1-(((4-methoxybenzyl)oxy)imino)propyl)pyridin-2-yl)oxy)acetic acid

Example 68

2-((5-(1-(((4-fluorobenzyl)oxy)imino)propyl)pyridin-2-yl)oxy)acetic acid

Example 69

2-((5-(1-(((4-cyanobenzyl)oxy)imino)propyl)pyridin-2-yl)oxy)acetic acid

Example 70

2-((5-(2-phenyl-1-(((4-(trifluoromethyl)benzyl)oxy)imino)ethyl)pyridin-2-yl)oxy)acetic acid

Example 71

2-((5-(2-phenyl-1-(((4-(trifluoromethyl)benzyl)oxy)imino)ethyl)pyridin-2-yl)oxy)-N-((tetrahydro-2H-pyran-4-yl)methyl)acetamide

Example 72

2-((5-(2-phenyl-1-(((4-(trifluoromethyl)benzyl)oxy)imino)ethyl)pyridin-2-yl)amino)acetic acid

Example 73

2-((5-(2-phenyl-1-(((4-(trifluoromethyl)benzyl)oxy)imino)ethyl)pyridin-2-yl)amino)-N-((tetrahydro-2H-pyran-4-yl)methyl)acetamide

Example 74

N-((tetrahydro-2H-pyran-4-yl)methyl)-2-((3-((((4-(trifluoromethyl)benzyl)oxy)imino)methyl)-1H-indol-5-yl)oxy)acetamide

Example 75

2-((3-((((4-(trifluoromethyl)benzyl)oxy)imino)methyl)-1H-indol-5-yl)oxy)acetic acid

Example 76

N-((tetrahydro-2H-pyran-4-yl)methyl)-2-((3-(1-(((4-(trifluoromethyl)benzyl)oxy)imino)ethyl)-1H-indol-5-yl)oxy)acetamide

Example 77

2-((3-(1-(((4-(trifluoromethyl)benzyl)oxy)imino)ethyl)-1H-indol-5-yl)oxy)acetic acid

Example 78

N-((tetrahydro-2H-pyran-4-yl)methyl)-2-((3-(1-(((4-(trifluoromethyl)benzyl)oxy)imino)propyl)-1H-indol-5-yl)oxy)acetamide

Example 79

2-((3-(1-(((4-(trifluoromethyl)benzyl)oxy)imino)propyl)-1H-indol-5-yl)oxy)acetic acid

Example 80

2-((3-(2-phenyl-1-(((4-(trifluoromethyl)benzyl)oxy)imino)ethyl)-1H-indol-5-yl)oxy)-N-((tetrahydro-2H-pyran-4-yl)methyl)acetamide

Example 81

2-((3-(2-phenyl-1-(((4-(trifluoromethyl)benzyl)oxy)imino)ethyl)-1H-indol-5-yl)oxy)acetic acid

Example 82

N-((tetrahydro-2H-pyran-4-yl)methyl)-3-(5-(1-(((4-(trifluoromethyl)benzyl)oxy)imino)ethyl)pyrimidin-2-yl)propanamide

Example 83

3-(5-(1-(((4-(trifluoromethyl)benzyl)oxy)imino)ethyl)pyrimidin-2-yl)propanoic acid

Example 84

N-((tetrahydro-2H-pyran-4-yl)methyl)-3-(5-(1-(((4-(trifluoromethyl)benzyl)oxy)imino)propyl)pyrimidin-2-yl)propanamide

Example 85

3-(5-(1-(((4-(trifluoromethyl)benzyl)oxy)imino)propyl)pyrimidin-2-yl)propanoic acid

Example 86

3-(5-(2-phenyl-1-(((4-(trifluoromethyl)benzyl)oxy)imino)ethyl)pyrimidin-2-yl)-N-((tetrahydro-2H-pyran-4-yl)methyl)propanamide

Example 87

3-(5-(2-phenyl-1-(((4-(trifluoromethyl)benzyl)oxy)imino)ethyl)pyrimidin-2-yl)propanoic acid

Example 88

N-((tetrahydro-2H-pyran-4-yl)methyl)-2-((5-(1-(((4-(trifluoromethyl)benzyl)oxy)imino)propyl)quinolin-8-yl)oxy)acetamide

Example 89

2-((5-(1-(((4-(trifluoromethyl)benzyl)oxy)imino)propyl)quinolin-8-yl)oxy)acetic acid

Example 90

2-((5-(2-phenyl-1-(((4-(trifluoromethyl)benzyl)oxy)imino)ethyl)quinolin-8-yl)oxy)-N-((tetrahydro-2H-pyran-4-yl)methyl)acetamide

Example 91

2-((5-(2-phenyl-1-(((4-(trifluoromethyl)benzyl)oxy)imino)ethyl)quinolin-8-yl)oxy)acetic acid The compounds of the present invention lowered LDL, triglyceride and total cholesterol. This was demonstrated by in vitro as well as in vivo animal experiments.

A) Demonstration of In Vitro Efficacy of Compounds

The in vitro binding assay described hereinafter is a quantitative solid phase binding assay for determining the efficacy of the compounds. Plates were pre-coated with a recombinant LDLR-AB domain, which binds to the gene pro-protein convertase of the subtype nine. Test compound at different concentrations was added to the subtype gene and added to LDLR immobilized on the wells. The amount of bound gene is measured by binding it with biotinylated anti-His-tag monoclonal antibody, followed by binding with horseradish peroxidase conjugated streptavidin substrate. The color was quantified by ELISA reader at 450 nM which reflects the relative amount of "the gene" that binds to LDLR in presence and absence of the inhibitor. $EC_{50}$ values were calculated by nonlinear regression analysis using graph pad prism software. Each concentration point represents values in duplicates.

| Example No | Concentration (μM) | % Inhibition |
|---|---|---|
| 1 | 1 | 29 |
|   | 10 | 35 |
|   | 100 | 57 |
| 3 | 1 | 28 |
|   | 10 | 41 |
|   | 100 | 54 |
| 4 | 1 | 34 |
|   | 10 | 39 |
|   | 100 | 51 |
| 5 | 1 | 34 |
|   | 10 | 40 |
|   | 100 | 50 |
| 10 | 1 | 3 |
|   | 5 | 18 |
|   | 10 | 35 |
|   | 100 | 51 |
| 11 | 1 | 20 |
|   | 5 | 23 |
|   | 10 | 49 |
|   | 100 | 61 |
| 12 | 1 | 19 |
|   | 10 | 55 |
|   | 100 | 79 |
| 13 | 1 | 22 |
|   | 10 | 32 |
|   | 100 | 48 |
| 14 | 1 | 15 |
|   | 10 | 31 |
|   | 100 | 41 |
| 15 | 1 | 25 |
|   | 10 | 37 |
|   | 100 | 39 |
| 16 | 1 | 10 |
|   | 5 | 21 |
|   | 10 | 35 |
|   | 100 | 61 |
| 17 | 1 | 13 |
|   | 10 | 19 |
|   | 100 | 44 |
| 18 | 1 | 16 |
|   | 10 | 38 |
|   | 100 | 63 |
| 19 | 10 | 40 |
|   | 100 | 46 |
| 20 | 1 | 20 |
|   | 10 | 34 |
|   | 100 | 57 |
| 21 | 100 | 15 |
| 22 | 1 | 29 |
|   | 10 | 46 |
|   | 100 | 46 |
| 23 | 1 | 30 |
|   | 10 | 42 |
|   | 100 | 47 |
| 24 | 1 | 24 |
|   | 10 | 28 |
|   | 100 | 52 |
| 25 | 1 | 28 |
|   | 10 | 34 |
|   | 100 | 50 |
| 26 | 1 | 45 |
|   | 10 | 45 |
|   | 100 | 52 |
| 27 | 1 | 10 |
|   | 10 | 15 |
|   | 100 | 29 |
| 28 | 100 | 23 |
| 30 | 100 | 36 |
| 31 | 1 | 15 |
|   | 10 | 20 |
|   | 100 | 29 |
| 32 | 1 | 14 |
|   | 10 | 35 |
|   | 100 | 48 |
| 33 | 1 | 10 |
|   | 10 | 10 |
|   | 100 | 28 |
| 34 | 1 | 7 |
|   | 10 | 13 |
|   | 100 | 32 |
| 35 | 1 | 22 |
|   | 10 | 13 |
|   | 100 | 25 |
| 36 | 1 | 6 |
|   | 10 | 9 |
|   | 100 | 36 |
| 37 | 1 | 20 |
|   | 10 | 26 |
|   | 100 | 28 |
| 38 | 10 | 19 |
|   | 100 | 38 |
| 39 | 10 | 33 |
|   | 100 | 42 |
| 40 | 10 | 20 |
|   | 100 | 47 |
| 41 | 1 | 10 |
|   | 100 | 19 |
| 42 | 10 | 9 |
|   | 100 | 51 |
| 43 | 10 | 15 |
|   | 100 | 27 |
| 48 | 1 | 17 |
|   | 10 | 42 |
|   | 100 | 64 |
| 49 | 10 | 7 |
|   | 100 | 11 |

B) LDL-C Lowering Activity—In High Fat Diet C57 Mice

The in-vivo LDL-c lowering for test compound was tested in C57 mice which were kept on high fat diet for 4 weeks and the blood was collected by retro-orbital sinus puncture method under light ether anesthesia on day 0 (pretreatment). Animal are grouped based on LDL-C levels, after that 4-6 week treatment with vehicle or test compound orally at a dose of 30 mpk dose once a day was given. On completion of treatment on day 28 of the treatment the blood was collected for LDL-C levels measurement. The percent change in LDL-C in test compound group Vs Vehicle group was calculated.

| Example | | % Change Vs Vehicle Control | |
|---|---|---|---|
| No | Dose | LDL-C | TC |
| 1 | 30 mg | −48.8 ± 4.2 | −11.8 ± 2.7 |
| 3 | 30 mg | −74.6 ± 2.0 | −33.6 ± 2.0 |
| 18 | 30 mg | −75.2 ± 3.5 | −41.6 ± 1.9 |
| 22 | 30 mg | −64.6 ± 4.1 | −21.5 ± 2.8 |
| 31 | 30 mg | −30.6 ± 3.6 | −3.5 ± 3.4 |

In certain instances, it may be appropriate to administer at least one of the compounds described herein or a pharmaceutically acceptable salt, ester, or prodrug thereof in combination with another therapeutic agent. Several reasons can be attributed for using a combination therapy depending on the need of the patient. As an example, if one of the side effects experienced by a patient upon receiving one of the compounds herein is hypertension, then it may be appropriate to administer an anti-hypertensive agent in combination with the initial therapeutic agent. Or, by way of example only, the benefit experienced by a patient may be increased by administering one of the compounds described herein with another therapeutic agent (which also includes a therapeutic regimen) that also has therapeutic benefit. Several such instances are well known to a skilled person and the use of combination therapy may be envisaged for all such situations. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds disclosed herein with agents found in the following pharmacotherapeutic classifications as indicated below. These lists should not be construed to be closed, but should instead serve as illustrative examples common to the relevant therapeutic area at present. Moreover, combination regimens may include a variety of routes of administration and should include oral, intravenous, intraocular, subcutaneous, dermal, and inhaled topical.

For the treatment of metabolic disorders, compounds disclosed herein may be administered with an agent selected from the group comprising: insulin, insulin derivatives and mimetics, insulin secretagogues, insulin sensitizers, biguanide agents, alpha-glucosidase inhibitors, insulinotropic sulfonylurea receptor ligands, meglitinides, GLP-1 (glucagon like peptide-1), GLP-1 analogs, DPPIV (dipeptidyl peptidase IV) inhibitors, GPR-119 inhibitors, sodium-dependent glucose co-transporter (SGLT2) inhibitors, PPAR modulators, non-glitazone type PPAR.delta. agonist, HMG-CoA reductase inhibitors, cholesterol-lowering drugs, rennin inhibitors, anti-thrombotic and anti-platelet agents and anti-obesity agents.

For the treatment of metabolic disorders, compounds disclosed herein may be administered with an agent selected from the group comprising: insulin, metformin, Glipizide, glyburide, Amaryl, gliclazide, meglitinides, nateglinide, repaglinide, amylin mimetics (for example, pramlintide), acarbose, miglitol, voglibose, Exendin-4, vildagliptin, Liraglutide, naliglutide, saxagliptin, pioglitazone, rosiglitazone, HMG-CoA reductase inhibitors (for example, rosuvastatin, atrovastatin, simvastatin, lovastatin, pravastatin, fluvastatin, cerivastatin, rosuvastatin, pitavastatin and like), cholesterol-lowering drugs (for example, fibrates which include: fenofibrate, benzafibrate, clofibrate, gemfibrozil and like; cholesterol absorption inhibitors such as Ezetimibe, eflucimibe etc.

From the foregoing description, one skilled in the art can easily ascertain the essential characteristics of this invention, and without departing from the spirit and scope thereof, can make various changes and modifications of the invention to adapt it to various usages and conditions. Such different embodiments are also to be considered to be within the scope of the present invention.

We claim:
1. A compound of formula (I)

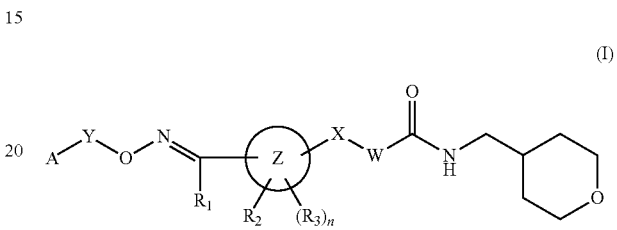

including its tautomeric form, its steroisomer, and its pharmaceutically acceptable salt.
  wherein 'A' represents an optionally substituted single or fused group selected from arly, heterocyclyl and cycloalky groups;
  wherein 'Y' represents either (i) a bond or (ii) a moiety selected from a substituted or unsubstituted, linear or branched $(C_1-C_6)$alkyl group, a substituted or unsubstituted, linear or branched $(C_2-C_6)$alkenyl group, and a group represented by '—U(CH$_2$)$_m$-' wherein U represents a moiety selected from O, $S(O)_o$, and NR$_4$ and 'm' represents integers from 2 to 4, and wherein 'o' in $S(O)_o$ represents an integer from 0 to 2 and R$_4$ in NR$_4$ represents a moiety selected from H and a substituted or unsubstituted linear or branched $(C_1-C_6)$alkyl group;
  wherein 'Z' represents an optionally substituted single or fused group selected from aryl, heterocyclyl and cycloalkyl groups;
  wherein 'X' represents either (i) a bond, or (ii) is selected from O, $S(O)_o$ or NR$_4$; wherein 'o' in $S(O)_o$ represents an integer from 0 to 2 and R$_4$ in NR$_4$ is a moiety slected from H and a substituted or unsubstituted linear or branched $(C_1-C_6$alkyl group;
  wherein 'W' represents a moiety selected from a substituted or unsubstituted linear or branched $(C_1-C_6)$alkyl group, and a substituted or unsubstituted linear or branched $(C_2-C_6)$ alkenyl group;
  wherein R$_1$ represents hydrogen, or a group selected from a $(C_1-C_6)$alkyl, $(C_3-C_6)$cycloalkyl, alkoxyalkyl, hydroxyalkyl, aminoalkyl, aryl, heterocyclyl, aralkyl, and heterocyclylalkyl, each of which may be optionally substituted; R$_2$ represents hydrogen, or a group selected from $(C_1-C_6)$alkyl, aryl, heterocyclyl, aralkyl, heterocyclylalkyl, $(C_1-C_6)$alkoxy, hydroxyalkyl, thio$(C_1-C_6)$alkyl, amino, aminoalkyl, and alkylamino, each of which may be optionally substituted; with the proviso that R$_1$ and R$_2$ together may optionally form a 4 to 7 membered saturated or partially saturated ring containing from 0-2 additional heteroatoms selected from the group of N, O, and $S(O)_o$, wherein 'o' in $S(O)_o$ represents an integer from 0 to 2; R$_3$ at each occurrence independently represents a moiety selected from hydrogen, halogen, an $(C_1-C_3)$alkyl group, a halo$(C_1-C_3)$alkyl group, a (C₁-C₃)alkoxy group, a thio(C₁-C₃)alkyl group, a sulfenyl derivative, and a sulfonyl derivative; and wherein 'n' represents integer from 0-3.

2. The compound as claimed in claim 1 wherein 'A' is selected from an optionally substituted aryl group or an optionally substituted heterocyclyl group.

3. The compound as claimed in claim 1 wherein when 'A' represents an aryl group, the aryl group being selected from a substituted or unsubstituted monocyclic or bicyclic aromatic group.

4. The compound as claimed in claim 3 wherein the aryl group is an optionally substituted phenyl group.

5. The compound as claimed in claim 1 wherein when 'A' represents a heterocyclyl group, the heterocyclyl group is selected from a single or fused, mono, bi or tricyclic aromatic or non-aromatic group containing one or more hetero atoms selected from O, N or S.

6. The compound as claimed in 5 wherein the heterocyclyl group is selected from a pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynyl, naphthylidinyl, purinyl, carbazolyl, phenothiazinyl, phenoxazinyl, benzoxazolyl, benzothiazolyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, and thieno piperidinyl group.

7. The compound as claimed in claim 1 wherein Z represents a group selected from an optionally substituted aryl group an optionally substituted heterocyclyl group.

8. The compound as claimed in claim 7 wherein the aryl group is selected from a substituted or unsubstituted monocyclic or bicyclic aromatic group.

9. The compound as claimed in claim 8 wherein the aryl group is an optionally substituted phenyl group.

10. The compound as claimed in claim 7 wherein the heterocyclyl group is selected from a single or fused mono or bi cyclic aromatic group containing one or more hetero atoms selected from O, N or S.

11. The compound as claimed in claim 10 wherein the aromatic heterocyclic group is selected from a pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynyl, naphthylidinyl, purinyl, carbazolyl, phenothiazinyl, phenoxazinyl, benzoxazolyl, and benzothiazolyl group.

12. The compound as claimed in claim 1 selected from
N-((tetrahydro-2H-pyran-4-yl)methyl)-2-(4-(1-(((4-(trifluoromethyl)benzyl)oxy)imino)propyl)phenoxy)acetamide;
N-((tetrahydro-2H-pyran-4-yl)methyl)-2-((5-(1-(((4-(trifluoromethyl) benzyl)oxy)imino)ethyl)pyridin-2-yl)oxy)acetamide;
N-((tetrahydro-2H-pyran-4-yl)methyl)-2-((5-(1-(((4-(trifluoromethyl) benzyl)oxy)imino)ethyl)pyridin-2-yl)amino)acetamide;
N-((tetrahydro-2H-pyran-4-yl)methyl)-2-((4-(1-(((4-(trifluoromethyl)benzyl)oxy)imino)propyl)phenyl)amino)acetamide;
2,2'-((5-(1-(((4-(trifluoromethyl)benzyl)oxy)imino)ethyl)oxazol-2-yl)azanediyl)bis(N-((tetrahydro-2H-pyran-4-yl)methyl)acetamide);
N-((tetrahydro-2H-pyran-4-yl)methyl)-2-((1-(4-(trifluoromethyl)benzyl)-3-((((4-(trifluoromethyl)benzyl)oxy)imino)methyl)-1H-indol-5-yl)oxy)acetamide;
2-(2-methyl-4-(2-phenyl-1-(((4-(trifluoromethyl)benzyl)oxy)imino)ethyl)phenoxy)-N-((tetrahydro-2H-pyran-4-yl)methyl)acetamide;
2-(4-(2-phenyl-1-(((4-(trifluoromethyl)benzyl)oxy)imino)ethyl)phenoxy)-N-((tetrahydro-2H-pyran-4-yl)methyl)acetamide;
2-(4-(2-phenyl-1-(((3-(trifluoromethyl)benzyl)oxy)imino)ethyl)phenoxy)-N-((tetrahydro-2H-pyran-4-yl)methyl)acetamide;
2-(4-(2-(pyridin-4-yl)-1-(((4-(trifluoromethyl)benzyl)oxy)imino)ethyl)phenoxy)-N-((tetrahydro-2H-pyran-4-yl)methyl)acetamide;
2-(4-(2-morpholino-1-(((4-(trifluoromethyl)benzyl)oxy)imino)ethyl)phenoxy)-N-((tetrahydro-2H-pyran-4-yl)methyl)acetamide;
N-((tetrahydro-2H-pyran-4-yl)methyl)-2-(4-(2-thiomorpholino-1-(((4-(trifluoromethyl)benzyl)oxy)imino)ethyl)phenoxy)acetamide;
2-(2-methyl-4-(2-(thiophen-3-yl)-1-(((4-(trifluoromethyl)benzyl)oxy)imino)ethyl)phenoxy)-N-((tetrahydro-2H-pyran-4-yl)methyl)acetamide;
N-((tetrahydro-2H-pyran-4-yl)methyl)-2-(4-((((4-(trifluoromethyl) benzyl)oxy)imino)methyl)phenoxy)acetamide;
N-((tetrahydro-2H-pyran-4-yl)methyl)-2-(4-(1-(((4-(trifluoromethyl)benzyl)oxy)imino)ethyl)phenoxy)acetamide;
N-((tetrahydro-2H-pyran-4-yl)methyl)-2-((5-((((4-(trifluoromethyl) benzyl)oxy)imino)methyl)pyridin-2-yl)oxy)acetamide;
N-((tetrahydro-2H-pyran-4-yl)methyl)-2-((4-(1-(((4-(trifluoromethyl) benzyl)oxy)imino)ethyl)phenyl)amino)acetamide;
2-((5-(1-(((4-cyanobenzyl)oxy)imino)ethyl)pyridin-2-yl)oxy)-N-((tetrahydro-2H-pyran-4-yl)methyl)acetamide;
N-((tetrahydro-2H-pyran-4-yl)methyl)-2-((5-(1-(((4-(trifluoromethyl)benzyl)oxy)imino)propyl)pyridin-2-yl)oxy)acetamide;
N-((tetrahydro-2H-pyran-4-yl)methyl)-2-((5-(1-(((4-(trifluoromethyl)benzyl)oxy)imino)propyl)pyridin-2-yl)amino)acetamide;
2-((5-(1-((benzyloxy)imino)propyl)pyridin-2-yl)oxy)-N-((tetrahydro-2H-pyran-4-yl)methyl)acetamide;
2-((5-(1-(((4-methylbenzyl)oxy)imino)propyl)pyridin-2-yl)oxy)-N-((tetrahydro-2H-pyran-4-yl)methyl)acetamide;
2-((5-(1-(((4-methoxybenzyl)oxy)imino)propyl)pyridin-2-yl)oxy)-N-((tetrahydro-2H-pyran-4-yl)methyl)acetamide;
2-((5-(1-(((4-fluorobenzyl)oxy)imino)propyl)pyridin-2-yl)oxy)-N-((tetrahydro-2H-pyran-4-yl)methyl)acetamide;
2-((5-(1-(((4-cyanobenzyl)oxy)imino)propyl)pyridin-2-yl)oxy)-N-((tetrahydro-2H-pyran-4-yl)methyl)acetamide;

2-(2-methyl-4-(1-(((4-(trifluoromethyl)benzyl)oxy)imino)butyl)phenoxy)-N-((tetrahydro-2H-pyran-4-yl)methyl)acetamide;
2-(4-(2-methoxy-1-(((4(trifluoromethyl)benzyl)oxy)imino)ethyl)phenoxy)-N-((tetrahydro-2H-pyran-4-yl)methyl)acetamide;
2-(4-(2-hydroxy-1-(((4-(trifluoromethyl)benzyl)oxy)imino)ethyl)phenoxy)-N-((tetrahydro-2H-pyran-4-yl)methyl)acetamide;
2-(2-methyl-4-(1-(((4-methylbenzyl)oxy)imino)-2-phenylethyl)phenoxy)-N-((tetrahydro-2H-pyran-4-yl)methyl)acetamide;
2-(4-(1-(((4-methylbenzyl)oxy)imino)-2-phenylethyl)phenoxy)-N-((tetrahydro-2H-pyran-4-yl)methyl)acetamide;
2-(4-(1-(((4-fluorobenzyl)oxy)imino)-2-phenylethyl)-2-methylphenoxy)-N-((tetrahydro-2H-pyran-4-yl)methyl)acetamide;
2-(4-(1-(((4-fluorobenzyl)oxy)imino)-2-phenylethyl)phenoxy)-N-((tetrahydro-2H-pyran-4-yl)methyl)acetamide;
2-(4-(1-(((4-chlorobenzyl)oxy)imino)-2-phenylethyl)-2-methylphenoxy)-N-((tetrahydro-2H-pyran-4-yl)methyl)acetamide;
2-(4-(1-(((4-chlorobenzyl)oxy)imino)-2-phenylethyl)phenoxy)-N-((tetrahydro-2H-pyran-4-yl)methyl)acetamide;
2-(2-methyl-4-(2-phenyl-1-(((4-(trifluoromethoxy)benzyl)oxy)imino)ethyl)phenoxy)-N-((tetrahydro-2H-pyran-4-yl)methyl)acetamide;
2-(4-(2-phenyl-1-(((4-trifluoromethoxy)benzyl)oxy)imino)ethyl)phenoxy)-N-((tetrahydro-2H-pyran-4-yl)methyl)acetamide;
2-(4-(1-(((4-methoxybenzyl)oxy)imino)-2-phenylethyl)-2-methylphenoxy)-N-((tetrahydro-2'-1-pyran-4-yl)methyl)acetamide;
2-(4-(1-(((4-methoxybenzyl)oxy)imino)-2-phenylethyl)phenoxy)-N-((tetrahydro-2H-pyran-4-yl)methyl)acetamide;
2-(4-(1-(((4-(methylsulfonyl)benzyl)oxy)imino)propyl)phenoxy)-N-((tetrahydro-2H-pyran-4-yl)methyl)acetamide;
2-(4-(2-phenyl-1-((pyridin-2-ylmethoxy)imino)ethyl)phenoxy)-N-((tetrahydro-2H-pyran-4-yl)methyl)acetamide;
2-(4-(1-((2-(1H-indol-1-yl)ethoxy)imino)propyl)phenoxy)-N-((tetrahydro-2H-pyran-4-yl)methyl)acetamide;
2-(4-(1-(((5-ethylpyrimidin-2-yl)oxy)imino)propyl)phenoxy)-N-((tetrahydro-2H-pyran-4-yl)methyl)acetamide;
2-(4-(1-(((5-methyl-2-phenyloxazol-4-yl)methoxy)imino)propyl)phenoxy)-N-((tetrahydro-2H-pyran-4-yl)methyl)acetamide;
2-(4-(1-(((3-(tert-butyl)-1-(p-tolyl)-1H-pyrazol-5-yl)methoxy)imino)propyl)phenoxy)-N-((tetrahydro-2H-pyran-4-yl)methyl)acetamide;
N-((tetrahydro-2H-pyran-4-yl)methyl)-2-((5-(((4-(trifluoromethyl)benzyl)oxy)imino)-5,6,7,8-tetrahydronaphthalen-2-yl)oxy)acetamide;
2-((5-(((4-chlorobenzyl)oxy)imino)-5,6,7,8-tetrahydronaphthalen-2-yl)oxy)-N-((tetrahydro-2H-pyran-4-yl)methyl)acetamide;
2-((5-(((4-cyanobenzyl)oxy)imino)-5,6,7,8-tetrahydronaphthalen-2-yl)oxy)-N-((tetrahydro-2H-pyran-4-yl)methyl)acetamide;
2-((5-(((4-methoxybenzyl)oxy)imino)-5,6,7,8-tetrahydronaphthalen-2-yl)oxy)-N-((tetrahydro-2H-pyran-4-yl)methyl)acetamide;
Methyl 3-(((((6-(2-oxo-2-(((tetrahydro-2H-pyran-4-yl)methyl)amino)ethoxy)-3,4-dihydronaphthalen-1(2H)-ylidene)amino)oxy)methyl)benzoate;
N-((tetrahydro-2H-pyran-4-yl)methyl)-2-((5-(1-(((4-(trifluoromethyl)benzyl)oxy)imino)ethyl)quinolin-8-yl)oxy)acetamide;
2-methyl-N-((tetrahydro-2H-pyran-4-yl)methyl)-2-(4-(1-(((4-(trifluoromethyl)benzyl)oxy)imino)propyl)phenoxy)propanamide;
2-methyl-N-((tetrahydro-2H-pyran-4-yl)methyl)-2-(4-(1-(((4-(trifluoromethyl)benzyl)oxy)imino)ethyl)phenoxy)propanamide;
2-(4-(1-(((tetrahydro-2H-pyran-4-yl)methoxy)imino)ethyl)phenoxy)-N-((tetrahydro-2H-pyran-4-yl)methyl)acetamide;
2-(4-(1-((cyclohexylmethoxy)imino)ethyl)phenoxy)-N-((tetrahydro-2H-pyran-4-yl)methyl)acetamide;
2-(4-(1-((naphthalen-2-ylmethoxy)imino)ethyl)phenoxy)-N-((tetrahydro-2H-pyran-4-yl)methyl)acetamide;
2-((5-(2-phenyl-1-(((4-(trifluoromethyl)benzyl)oxy)imino)ethyl)pyridin-2-yl)oxy)-N-((tetrahydro-2H-pyran-4-yl)methyl)acetamide;
2-((5-(2-phenyl-1-(((4-(trifluoromethyl)benzyl)oxy)imino)ethyl)pyridin-2-yl)amino)-N-((tetrahydro-2H-pyran-4-yl)methyl)acetamide;
N-((tetrahydro-2H-pyran-4-yl)methyl)-2-((3-((((4-(trifluoromethyl)benzyl)oxy)imino)methyl)-1H-indol-5-yl)oxy)acetamide;
N-((tetrahydro-2H-pyran-4-yl)methyl)-2-((3-(1-(((4-(trifluoromethyl)benzyl)oxy)imino)ethyl)-1H-indol-5-yl)oxy)acetamide;
N-((tetrahydro-2H-pyran-4-yl)methyl)-2-((3-(1-(((4-(trifluoromethyl)benzyl)oxy)imino)propyl)-1H-indol-5-yl)oxy)acetamide;
2-((3-(2-phenyl-1-(((4-(trifluoromethyl)benzyl)oxy)imino)ethyl)-1H-indol-5-yl)oxy)-N-((tetrahydro-2H-pyran-4-yl)methyl)acetamide;
N-((tetrahydro-2H-pyran-4-yl)methyl)-3-(5-(1-(((4-(trifluoromethyl)benzyl)oxy)imino)ethyl)pyrimidin-2-yl)propanamide;
N-((tetrahydro-2H-pyran-4-yl)methyl)-3-(5-(1-(((4-(trifluoromethyl)benzyl)oxy)imino)propyl)pyrimidin-2-yl)propanamide;
3-(5-(2-phenyl-1-(((4-(trifluoromethyl)benzyl)oxy)imino)ethyl)pyrimidin-2-yl)-N-((tetrahydro-2H-pyran-4-yl)methyl)propanamide;
N-((tetrahydro-2H-pyran-4-yl)methyl)-2-((5-(1-(((4-(trifluoromethyl)benzyl)oxy)imino)propyl)quinolin-8-yl)oxy)acetamide; and
2-((5-(2-phenyl-1-(((4-(trifluoromethyl)benzyl)oxy)imino)ethyl)quinolin-8-yl)oxy)-N-((tetrahydro-2H-pyran-4-yl)methyl)acetamide.

13. A pharmaceutical composition containing the compound as claimed in claim 1.

14. A pharmaceutical composition for the treatment of hyperlipidemia, dyslipidemia and other similar diseases comprising the compound of formula (I) as claimed in claim 1 and at least one pharmaceutically active agent.

15. A pharmaceutical composition as claimed in claim 13, further comprising at least one pharmaceutically active agent selected from the group consisting of insulin, insulin derivatives and mimetics, insulin secretagogues, insulin sensitizers, biguanide agents, alpha-glucosidase inhibitors, insulinotropic sulfonylurea receptor ligands, meglitinides, GLP-1 (glucagon like peptide-1), GLP-1 analogs, DPPIV (dipeptidyl peptidase IV) inhibitors, GPR-119 activators, sodium-dependent glucose co-transporter (SGLT2) inhibitors, PPAR modulators, non-glitazone type PPAR delta agonist, HMG-CoA reductase inhibitors, cholesterol-lowering drugs, rennin inhibitors, anti-thrombotic and anti-platelet agents and anti-obesity agents and pharmaceutically acceptable salts thereof.

16. An intermediate for the preparation of compound of formula (I) as claimed in claim 1 selected from

- 2-((5-(1-(((4-(trifluoromethyl)benzyl)oxy)imino)ethyl)pyridin-2-yl)oxy)acetic acid;
- 2,2'-((5-(1-(((4-(trifluoromethyl)benzyl)oxy)imino)ethyl)oxazol-2-yl)azanediyl)diacetic acid;
- 2-((1-(4-(trifluoromethyl)benzyl)-3-((((4-(trifluoromethyl)benzyl)oxy)imino)methyl)-1H-indol-5-yl)oxy)acetic acid;
- 2-((5-(1-(((4-(trifluoromethyl)benzyl)oxy)imino)ethyl)quinolin-8-yl)oxy)acetic acid;
- 2-((5-(1-(((4-(trifluoromethyl)benzyl)oxy)imino)ethyl)pyridin-2-yl)amino)acetic acid;
- 2-((5-((((4-(trifluoromethyl)benzyl)oxy)imino)methyl)pyridin-2-yl)oxy)acetic acid;
- 2-((5-(1-(((4-cyanobenzyl)oxy)imino)ethyl)pyridin-2-yl)oxy)acetic acid;
- 2-((5-(1-(((4-(trifluoromethyl)benzyl)oxy)imino)propyl)pyridin-2-yl)oxy)acetic acid;
- 2-((5-(1-(((4-(trifluoromethyl)benzyl)oxy)imino)propyl)pyridin-2-yl)amino)acetic acid;
- 2-((5-(1-((benzyloxy)imino)propyl)pyridin-2-yl)oxy)acetic acid;
- 2-((5-(1-(((4-methylbenzyl)oxy)imino)propyl)pyridin-2-yl)oxy)acetic acid;
- 2-((5-(1-(((4-methoxybenzyl)oxy)imino)propyl)pyridin-2-yl)oxy)acetic acid;
- 2-((5-(1-(((4-fluorobenzyl)oxy)imino)propyl)pyridin-2-yl)oxy)acetic acid;
- 2-((5-(1-(((4-cyanobenzyl)oxy)imino)propyl)pyridin-2-yl)oxy)acetic acid;
- 2-((5-(2-phenyl-1-(((4-(trifluoromethyl)benzyl)oxy)imino)ethyl)pyridin-2-yl)oxy)acetic acid;
- 2-((5-(2-phenyl-1-(((4-(trifluoromethyl)benzyl)oxy)imino)ethyl)pyridin-2-yl)amino)acetic acid;
- 2-((3-((((4-(trifluoromethyl)benzyl)oxy)imino)methyl)-1H-indol-5-yl)oxy)acetic acid;
- 2-((3-(1-(((4-(trifluoromethyl)benzyl)oxy)imino)ethyl)-1H-indol-5-yl)oxy)acetic acid;
- 2-((3-(1-(((4-(trifluoromethyl)benzyl)oxy)imino)propyl)-1H-indol-5-yl)oxy)acetic acid;
- 2-((3-(2-phenyl-1-(((4-(trifluoromethyl)benzyl)oxy)imino)ethyl)-1H-indol-5-yl)oxy)acetic acid;
- 3-(5-(1-(((4-(trifluoromethyl)benzyl)oxy)imino)ethyl)pyrimidin-2-yl)propanoic acid;
- 3-(5-(1-(((4-(trifluoromethyl)benzyl)oxy)imino)propyl)pyrimidin-2-yl)propanoic acid;
- 3-(5-(2-phenyl-1-(((4-(trifluoromethyl)benzyl)oxy)imino)ethyl)pyrimidin-2-yl)propanoic acid;
- 2-((5-(1-(((4-(trifluoromethyl)benzyl)oxy)imino)propyl)quinolin-8-yl)oxy)acetic acid;
- 2-((5-(2-phenyl-1-(((4-(trifluoromethyl)benzyl)oxy)imino)ethyl)quinolin-8-yl)oxy)acetic acid.

* * * * *